US010287615B2

(12) United States Patent
Develter et al.

(10) Patent No.: US 10,287,615 B2
(45) Date of Patent: May 14, 2019

(54) SOPHOROLACTONE PRODUCTION

(75) Inventors: Dirk Develter, Maldegem (BE); Steve Fleurackers, Deurne (BE)

(73) Assignee: ECOVER CO-ORDINATION CENTER N.V., Malle (BE)

( * ) Notice: Subject to any disclaimer, the term of this patent is extended or adjusted under 35 U.S.C. 154(b) by 538 days.

(21) Appl. No.: 14/123,858

(22) PCT Filed: Jun. 6, 2012

(86) PCT No.: PCT/EP2012/060744
§ 371 (c)(1),
(2), (4) Date: Dec. 4, 2013

(87) PCT Pub. No.: WO2012/168325
PCT Pub. Date: Dec. 13, 2012

(65) Prior Publication Data
US 2014/0194336 A1  Jul. 10, 2014

(30) Foreign Application Priority Data

Jun. 6, 2011  (WO) ................ PCT/EP2011/059306
Jun. 6, 2011  (WO) ................ PCT/EP2011/059310

(51) Int. Cl.
| C07F 15/04 | (2006.01) |
| C07H 15/10 | (2006.01) |
| C12P 19/44 | (2006.01) |
| C12N 15/52 | (2006.01) |
| C12N 15/01 | (2006.01) |
| C07H 15/04 | (2006.01) |
| C12P 7/64 | (2006.01) |
| C12P 19/12 | (2006.01) |
| C11D 3/20 | (2006.01) |
| C12P 17/18 | (2006.01) |
| C11D 1/66 | (2006.01) |
| C07C 59/01 | (2006.01) |
| C11D 1/825 | (2006.01) |

(52) U.S. Cl.
CPC ............ *C12P 19/445* (2013.01); *C07C 59/01* (2013.01); *C07H 15/04* (2013.01); *C11D 1/662* (2013.01); *C11D 1/825* (2013.01); *C11D 3/2096* (2013.01); *C12N 15/01* (2013.01); *C12N 15/52* (2013.01); *C12P 7/64* (2013.01); *C12P 7/6436* (2013.01); *C12P 17/181* (2013.01); *C12P 19/12* (2013.01); *C12P 19/44* (2013.01)

(58) Field of Classification Search
CPC ............................... C07H 15/04; C07H 15/00
USPC ...................................................... 536/18.02
See application file for complete search history.

(56) References Cited

U.S. PATENT DOCUMENTS

| 5,559,089 A | 9/1996 | Edwards et al. |
| 5,654,192 A | 8/1997 | Ducreux et al. |
| 5,767,255 A * | 6/1998 | Wullbrandt ............ C07H 15/04 435/255.4 |
| 5,879,913 A * | 3/1999 | Marchal ................. C12P 19/44 435/100 |
| 6,596,779 B1 | 7/2003 | Jean-Noel et al. |
| 7,556,654 B1 | 7/2009 | Nero |
| 8,530,206 B2 * | 9/2013 | Develter ................ C12N 15/01 435/134 |
| 2004/0120911 A1 | 6/2004 | Shah et al. |
| 2004/0171512 A1 | 9/2004 | Furuta et al. |
| 2014/0113818 A1 | 4/2014 | Develter et al. |

FOREIGN PATENT DOCUMENTS

| CA | 2776029 A1 | 4/2011 |
| DE | 19749413 A1 * | 11/1997 |
| EP | 0209783 A1 | 1/1987 |
| EP | 0499434 A1 | 8/1992 |
| EP | 1411111 A1 * | 4/2004 |
| EP | 1445302 A1 | 8/2004 |
| EP | 1953237 A1 | 8/2008 |

(Continued)

OTHER PUBLICATIONS

Gorin et al. (Can. J. Chem. 1961, vol. 39, 846-855).*

(Continued)

*Primary Examiner* — Mina Haghighatian
*Assistant Examiner* — Mei Ping Chui
(74) *Attorney, Agent, or Firm* — Knobbe, Martens, Olson & Bear, LLP

(57) ABSTRACT

The present invention relates to a process for selectively producing sophorolactone without use of organic solvent, comprising the steps of: —pre-cultivating cells of a *Candida* species capable of producing sophorolactone, in absence of an oily substrate until a stationary growth phase is obtained, —cultivating said pre-cultivated cells in an aqueous medium in the presence of at least one fermentable sugar and substrate; the reaction mixture of sugar, substrate and pre-cultivated cells being present in an amount and conditions such that the cells metabolize the sugar and substrate thereby forming sophorolactone and fatty acid, —continuously feeding said substrate to said cells thereby suppressing the formation of fatty acid and keeping fatty acid levels in the reaction mixture below 10 g/l, resulting in the crystallization of at least part of the sophorolactone present in the reaction mixture, —warming the reaction mixture to a temperature between 60° C. and 90° C., thereby melting the sophorolactone crystals, —allowing the molten sophorolactone to settle and to provide a crude sophorolactone composition, and —removing the crude sophorolactone composition from the remainder of the reaction mixture without use of an organic solvent.

11 Claims, 7 Drawing Sheets

(56) References Cited

FOREIGN PATENT DOCUMENTS

| FR | 2740779 A1 | 5/1997 | | |
|---|---|---|---|---|
| FR | 2779057 A1 | 12/1999 | | |
| WO | WO 1999024448 A2 | * | 5/1999 | ............ A01N 43/16 |
| WO | WO 2004/044216 A1 | | 5/2004 | |
| WO | WO 2009/141407 A2 | * | 11/2009 | ............ C12N 15/10 |
| WO | WO 2010/050413 A1 | | 5/2010 | |
| WO | WO 2011/120776 A1 | | 10/2011 | |
| WO | WO 2011/127101 A1 | | 10/2011 | |

OTHER PUBLICATIONS

Bogaert et al. (Biotechnology and Bioengineering, vol. 108, No. 4, Apr. 2011, p. 734-741.*

International Search Report and Written Opinion of the International Searching Authority for International Application No. PCT/EP2012/060744, dated Aug. 3, 2012.

Ashby et al., "The use of fatty acid esters to enhance free acid sophorolipid synthesis," *Biotechnology Letters*, vol. 28(4), pp. 253-260 (2006).

Ashby et al., "The influence of increasing media methanol concentration on sophorolipid biosynthesis from glycerol-based feedstocks", *Biotechnology Letters*, vol. 32(10), pp. 1429-1437 (2010).

Cavalero et al., "The effect of medium composition on the structure and physical state of sophorolipids produced by *Candida bombicola* ATCC 22214," *Journal of Biotechnology*, vol. 103(1), pp. 31-41 (2003).

Felse et al., "Sophorolipid biosynthesis by *Candida bombicola* from industrial fatty acid residues," *Enzyme and Microbial Technology*, vol. 40(2), pp. 316-323 (2007).

Fleurackers, "On the use of waste frying oil in the synthesis of sophorolipids," *European Journal of Lipid Science and Technology*, vol. 108(1), pp. 5-12 (2006).

Rau et al., "Sophorolipids: a source for novel compounds," *Industrial Crops and Products*, vol. 13, pp. 85-92 (2001).

Solaiman et al., "Production of sophorolipids by *Candida bombicola* grown on soy molasses as substrate," *Biotechnology Letters*, vol. 26(15), pp. 1241-1245 (2004).

Van Bogaert et al., "Microbial production and application of sophorolipids," *Applied Microbiology and Biotechnology*, vol. 76, pp. 23-34 (2007).

Van Bogaert et al., "Production of New-to-Nature Sophorolipids by Cultivating the Yeast *Candida bombicola* on Unconventional Hydrophobic Substrates," *Biotechnology and Bioengineering*, vol. 108(4), pp. 734-741 (Apr. 2011).

Williams, "Biosurfactants for cosmetic application: Overcoming production challenges," *MMG 445 Basic Biotechnology*, vol. 5, pp. 78-83 (2009).

Hardin et al., Journal of Surgical Research, 2007, 142, 314-319.

Hu et al. "Purification of lactonic sophorolipids by crystallization" Journal of Biotechnology, vol. 87, pp. 263-272 (2001).

Brakemeier A. et al, Biotechnology letters, vol. 17, No. 11, Nov. 1995, p. 1183-1188.

Fleurackers S. J. J. et al, Eur. J. Lipid Sci. Technol. 2010 (112): 655-662.

* cited by examiner

SOPHOROLACTONE PRODUCTION

CROSS-REFERENCE TO RELATED APPLICATIONS

This application is the U.S. National Phase under 35 U.S.C. § 371 of International Application PCT/EP2012/060744, filed Jun. 6, 2012, which claims priority to PCT/EP2011/059306, filed Jun. 6, 2011 and PCT/EP2011/059310, filed Jun. 6, 2011.

TECHNICAL FIELD

The present invention relates to an improved process for the production of sophorolactone, to a sophorolactone composition in the form of a solid or paste obtainable by the method and to formulations comprising sophorolactone obtained by the method. In addition the present invention relates to processes for the manufacturing of derivatives of the sophorolactone, to the sophorolactone derivatives and to uses thereof.

BACKGROUND

Sophorolipids, formerly known as sophorosides, are glycolipid biosurfactants produced by yeast strains such as *Starmerella* (*Candida*) *bombicola*, *Candida apicola*, *Candida bogoriensis*, *Candida batistae* and *Wickerhamilella domercqiae*. They are composed of a disaccharide moiety linked to one hydroxyl group of one w or (w-1)-hydroxy fatty acid that is saturated or monounsaturated. The sugar moiety, i.e. sophorose or 2-O-glucopyranosyl-D-glucopyranose, may further show mono- or diacetylation at the 6' and 6" positions. The nature of the hydroxy fatty acid is characteristic, with the hydroxyl group being located on the n or n-1 carbon atom. The composition of the hydroxylated fatty acid varies depending on the production conditions. Lactonization frequently occurs between the carboxyl group and the 4" OH group of the sophorose, providing sophorolactones in addition to sophorolipids in acid form. Hence, sophorolipids are considered as being a mixture of the compounds presented by the formula I, representing sophorolipids in lactone form, and by formula II, representing sophorolipids in acid form, in which 1. R' and R'" represent hydrogen or an acetyl group, or 2. R' is an acetyl group and R'" a hydrogen group, or 3. R' is hydrogen and R" is an acetyl group, or 4. both R' and R" are hydrogen, or 5. both R' and R" are acetyl groups. The molecules of formula I are lactonic sophorolipids, also called sophorolactones. The molecules of formula II are open ring sophorolipids, also called sophorolipids in acid form. The carbon chain length n may range from 2 to 16 carbon atoms. Typically the carbon chain length is 16 to 18 carbons long; that is n=13-15.

Sophorolipids are typically produced by fermentation processes wherein a glycolipid producing micro-organism is fed with a sugar supply and a substrate under appropriate fermentation conditions for the production of the sought sophorolipids.

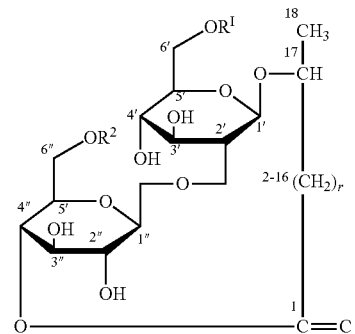

(I)

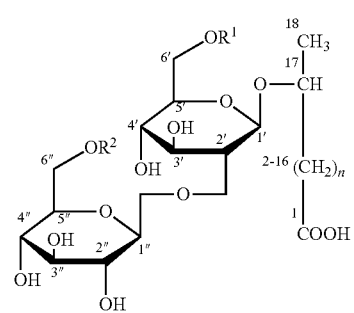

(II)

This process has the disadvantage that a group of numerous homologs is formed. Moreover the formation ratio of these homologs varies as a function of their substrate, e.g. a hydrocarbon source, as well as the fermentation conditions. The production of a product having a given ratio using a fermentation process is difficult. This also hampers product development as properties and function of the sophorolipid varies with ratios of the homologs.

It is known that the acetyl bonds in sophorolipids are chemically unstable and are very easily hydrolysed by heating or prolonged storage close to neutrality or even at ambient temperature under slightly alkaline conditions, which leads to the obtaining of the completely de-acetylated acid form. It is therefore extremely difficulty by fermentation or chemistry to obtain a single product and a fortiori an acetylated product.

Processes for the isolation of one of the main forms (acid or lactone) from sophorolipids have been investigated. The processes thus far described require extraction by alcohol, e.g. EP 209783, a process which is both long and expensive. Moreover extraction by a specific solvent does not always give good results, because the solubility of the homologues in a solvent differs significantly, which affects the quality of the products obtained. In addition, it is not desirable in view of the use of sophorolipids as biosurfactants. It is undesirable that the product contains traces of organic solvents, resulting from the separation process.

The lactone form of sophorolipids has been documented to be the most active sophorolipid type, both with regard to lowering surface tension and to antimicrobial activity.

Therefore there is a demand in the industry for an improved sophorolactone production process, which leads to less complex mixtures, is easy in use, provides a satisfactory yield, is economically feasible, and is environmentally friendly, e.g. less organic solvent use.

In the prior art, for instance EP1411111, a liquid sophorolipid mixture is formulated on an alkaline powder. This composition spontaneously hydrolysed during storage to sophorolipids in acid form. These acids are known for their increased foaming over sophorolipids in lactone form. As a result, the products produced increased amounts of foam when used. This is particularly undesirable in applications where foam formation needs to be controlled, for instance in automated dishwashers characterized by frequent mechanical actions. Hence, it would be desirable to obtain a sophorolactone composition with improved hydrolytic stability, and thus storage stability.

Furthermore, there is a demand in industry to obtain an economically feasible source of sophorolactone that allows the production of derivatives such as w or (w-1)-hydroxy fatty acids and/or sophorose on an economically relevant scale.

It is an object of the present invention to provide an improved process for the synthesis of sophorolactone and derivatives, that at least solves one of the problems of the prior art. It is a further object of the invention to provide sophorolactone compositions with improved properties, such as hydrolytic stability, increased ease of handling. It is also an object of the invention to provide a more economically friendly access to some uses of sophorolactone and its derivatives.

SUMMARY OF THE INVENTION

The present invention thereto provides an improved process for the selective production of sophorolactone in absence of an organic solvent comprising the steps of:
  pre-cultivating cells of a *Candida* species capable of producing sophorolactone, in absence of an oily substrate until a stationary growth phase is obtained,
  cultivating said pre-cultivated cells in an aqueous medium in the presence of at least one fermentable sugar and substrate; the reaction mixture of sugar, substrate and pre-cultivated cells being present in an amount and conditions such that the cells metabolize the sugar and substrate thereby forming sophorolactone and fatty acid,
  continuously feeding said substrate to said cells thereby suppressing the formation of fatty acid and keeping fatty acid levels in the reaction mixture below 10 g/l and thereby crystallizing at least part of the sophorolactone present in the reaction mixture,
  warming the reaction mixture to a temperature between 60° C. and 90° C., thereby melting the sophorolactone crystals,
  allowing the molten sophorolactone to settle and to provide a crude sophorolactone composition, and
  removing the crude sophorolactone composition from the remainder of the reaction mixture without use of an organic solvent.

The inventors have found that less acid sophorolipids are formed when the manufacturing process is split up over a step using a preculture without oil and a fermentation step using an oily substrate; and keeping fatty acid levels below a pre-determined level in the fermentation broth.

The method is also applicable to substrates other than oils, said other substrates including shielded esters, for instance as described in EP1953237, and alcohols, such as described in Brakemeier A. et al, Biotechnology letters, vol. 17, No. 11, nov. 1995, P1183-1188 or Fleurackers S. J. J. et al, Eur. J. Lipid Sci. Technol. 2010 (112): 655-662.

The decreased formation of acid sophorolipids has two advantages; first the envisaged lactone content will be higher and downstream processing easier. Secondly due to the lower content of acid sophorolipids, which foam more than sophorolactones, foam control will be easier. Hence the addition of antifoaming agents, which are difficult to remove later on, can be avoided. The fermenter capacity can thus be made maximal use of and a crude sophorolactone composition with low residual substrate content will result, allowing for lactone isolation. This provides access to sophorolactone in solid form, such as a powder, with improved hydrolytic stability due to the absence of water.

A process according to an embodiment of the invention has the advantage that it is straightforward, simple to execute and results in a less complex sophorolipid mixture than prior art procedures. It has for effect that high yields of sophorolactone are obtained. Suppression of the acid levels has for effect that no emulsion is formed and the lactone form will not be solubilized.

The aqueous process of the invention does not require the use of organic solvents to obtain sophorolactone. The resulting products are free of traces of organic solvent.

In a preferred embodiment of a process according to the invention, the process comprising the steps of:
  cooling the crude sophorolactone composition thereby producing a solid, such as a paste,
  dispersing the solid in water, preferably decalcified water, at a temperature of 5-25° C., preferably 10-15° C.; more preferably at 10° C., using a mass ratio of water to solid between 0.5 and 15; thereby obtaining an aqueous dispersion of sophorolactone crystals,
  separating the crystals from the water,
  repeating the dispersion and separation steps from 0 to 10 times keeping the temperature of the water below 40° C., preferably below 30° C.;
  drying the resulting sophorolactone composition thereby providing dried sophorolactone.

The above steps provide for a further separation of sophorolipids in acid form and in lactone form. Highly pure sophorolactone is obtained by a process according to an embodiment of the invention.

In a preferred embodiment of a process according to the invention, water is removed from the crystals prior to drying by melting the crystals to a temperature between 35° C. and 55° C., thereby providing a lower layer comprising sophorolactone and an upper layer of supernatant water; separating the lower layer from the upper layer to obtain a sophorolactone composition with increased active matter content.

In a preferred embodiment of a process as described above, the drying is by spray drying, drum drying, convection drying, thin film evaporation, vacuum drying, flaking, extruding or casting.

In a preferred embodiment of a process according to the invention, the sophorolactone composition separated off the reaction mixture is in the form of an aqueous sophorolipid mixture comprising at least 30 wt %, preferably at least 70 wt %; more preferably at least 80 wt % sophorolactone, expressed on the dry matter content of the aqueous sophorolipid mixture.

In a preferred embodiment of a process according to the invention, the sophorolactone is comprised in a composition comprising at most 60 weight percent water.

In a preferred embodiment of a process according to the invention, the fatty acid levels are suppressed by adjusting the level of substrate fed to the metabolizing cells.

In a preferred embodiment of a process according to the invention, the sugar and substrate are fed to the pre-cultivated cells in a fed batch mode.

In a preferred embodiment of a process according to the invention, the fatty acid level of the reaction mixture is suppressed below 10 g/l, preferably below 8 g/l, more preferably between 1-5 g/l, expressed in weight of acid per liter of reaction mixture.

In a preferred embodiment of a process according to the invention, the substrate comprises corn steep liquor.

In a preferred embodiment of a process according to the invention, the pre-cultivation is carried out in the absence of an oil.

In a preferred embodiment of a process according to the invention, the substrate is a triglyceride; preferably a triglyceride of saturated or unsaturated fatty acids with 16 or 18 carbon atoms; more preferably a vegetable oil; most preferably rapeseed oil.

In a preferred embodiment of a process according to the invention, the substrate is isostearic acid or isostearic alcohol, preferably isostearyl alcohol.

In a preferred embodiment of a process according to the invention, the substrate a shielded ester of formula H—$(CH_2)_n$—O—CO—$(CH_2)_m$—COOH with an carbon chain length of 16 to 18.

In a preferred embodiment of a process according to the invention, the substrate comprises a carbon chain length lower than C14, preferably between C8 and C14, and the fermentation medium comprises cells of a *Candida* species modified to improve the conversion of said substrate with short carbon chain length into sophorolactone.

In a preferred embodiment of a process according to the invention, the *Candida* is *Candida bombicola* mutant strain M18, M30 or M33; preferably *Candida bombicola* M30. In a preferred embodiment of a process according to the invention, the process additionally comprising the step of filtering the sophorolactone separated off the reaction mixture by depth filtration, more preferably by depth filtration at a temperature between 40° C. and 90° C. and pressure of between 0.5 bar and 2.5 bar; most preferably by depth filtration at a temperature between 60° C. and 70° C. and pressure between 0.5 and 2.0 bar.

In a preferred embodiment of a process according to the invention, the fermentation is executed in a vessel at an overpressure of between 0-1.5 bar, preferably at 0.5-0.6 bar. This allows control of foam formation.

In a further aspect the present invention provides a sophorolactone composition in the form of a solid or paste, obtainable by a method according to an embodiment of the invention, consisting of 60-70 wt % sophorolactone, 0-30 wt % sophorolipid acid, 0-1 wt % residual substrate including less than 0.2 wt % fatty acid, and remainder water.

By the term residual substrate it is meant the sum of the non-metabolised substrate and the metabolites other than sophorolipids thereof, i.e. triglycerides and fatty acids, fatty alcohol and fatty acid, methylesters and fatty acids or fatty acids as such.

In a preferred embodiment the sophorolactone composition obtainable by a method according to the invention comprises at least 60 weight percent sophorolactone and at most 40 weight percent water.

In a preferred embodiment the sophorolactone composition consists of 70-100 wt % sophorolipid lactone, 0-1 wt % sophorolipid acid, preferably 0-0.5% sophorolipid acid, less than 0.1% residual substrate including fatty acid, and remainder water.

In a third embodiment, the present invention provides a formulation obtained by dissolving the sophorolactone composition according to an embodiment of the invention in a solvent with a polarity parameter delta P between 5 and 9.5 and a hydrogen bonding parameter delta H between 8 and 15.

In a preferred embodiment, the solvent in a formulation according to an embodiment of the invention is selected from the list of phenoxyethanol, benzylalcohol, phenetyl alcohol, hydrocinnamylalcohol, tetrahydrofurfuryl alcohol, dimethylisosorbide, methyl salicylate and eugenol.

In a further aspect, the invention provides a dry solid product for laundry or dishwashing, comprising a sophorolactone composition consisting of 70-100 wt % sophorolipid lactone, 0-1 wt % sophorolipid acid, less than 0.1% residual substrate and remainder water; wherein the pH of the product is 8.0-14.0, preferably 8.5-11.50, as measured on a 1% solution of the product in water.

In a fifth aspect the invention provides a process for the preparation of partially hydrolysed sophorolactone comprising the steps of:
providing a sophorolactone or sophorolactone composition obtainable by a process according to an embodiment of the invention,
hydrolysing at least part of the sophorolactone, either by adding to the sophorolactone 0.5 to 1 equivalents of a base or by heating the sophorolactone for more than 4 hours, preferably more than 24 hours, to a temperature between 70-90° C., preferably between 80-90° C., thereby hydrolysing at least part of the sophorolactone to sophorolipid acid and its salt.

Suitable bases for use are potassium hydroxide, sodium hydroxide, magnesium hydroxide, ammonium hydroxide, monoethanolamine, guanidine or guanidinium hydroxide. The foam behavior and desired solubility of the product can be tuned by the amount of base equivalents used for the hydrolysation.

In a sixth aspect, the invention provides a method for the preparation of a ω hydroxy fatty acid of formula CH2OH—CH2-(CH2)n-COOH or a ω-1 hydroxy fatty acid of formula CH3-CHOH—(CH2)n-COOH, wherein the acid is derived from a sophorolipid, with n corresponding to an integer between 2 and 16, comprising the step of:
providing a sophorolactone or sophorolactone composition,
hydrolysing the sophorolactone to sophorolipid acid using a base,
separating the sugar moiety and the ω and ω-1 hydroxy fatty acid moiety of the sophorolipid acid; preferably by hydrolysis with a weak acid or by enzymatic reaction,
recovering the sugar moieties and/or the ω and ω-1 hydroxy fatty acid obtained.

This preparation method is advantageous as it provides sophorose. This is in contrast to an acid hydrolysis whereby the sophorose is lost.

In a preferred embodiment the hydroxy fatty acid is derived from isostearine acid.

In a preferred embodiment, the separation of the sophorolipid acid into a sugar moiety and ω and ω-1 hydroxy fatty acid moiety is by enzymatic reaction, preferably in the presence of endoglycoceramidase II recombinant (E.C. 3.2.1.123).

More preferably sophorolipid acids free of esteric bonds are used as starting material for the enzymatic reaction. This ensures ready access of the enzyme to the substrate. Alkaline hydrolysis of the sophorolactone followed with a suitable purification process such as crystallization in an acid pH would hydrolyze all esteric bonds but leave the glycosidic bonds intact. A 1% aqueous sophorolactone solution, expressed in weight of the sophorolactone by total weight of the solution, at a pH of 5.5 combined with 1.5 units of the endoglycoceramidase II enzyme is then reacted for at least 16 hours, preferably at least 24 hours, at a temperature of 37° C.

In a final aspect the invention provides hydroxy fatty acid obtained by a method according to an embodiment of the invention, characterized by the virtual absence of non hydroxylated fatty acids, meaning in a concentration below 0.1%.

FIGURES

FIG. 1 is a graphic representation of the results of solubility experiments of sophorolactones, expressed in Hansen solubility parameters delta H and delta P.

FIG. 2 is a graphic representation of the oil feeding rate corresponding with the experiment as described in Example 1. On the Y-axis the speed of addition of oil, expressed in g/h, and the amount of oil, expressed in g, are depicted on the left-hand side. On the right-hand side the residual amount of acid (g/l) is displayed. On the X-axis the duration of the process is displayed, expressed in hours. Residual oil levels are monitored and kept below a pre-determined level of 8 g/l.

Figure 8:
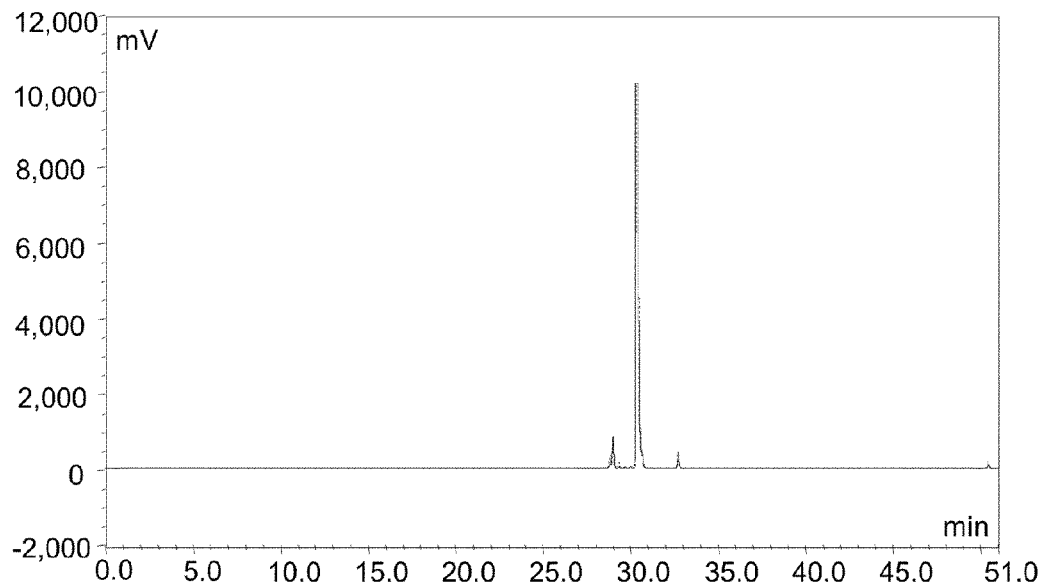

FIG. 8 is graphic representation of a chromatogram recorded on a non-aqueous sophorolactone solution prior to storage (black curve) and after storage (grey curve) at 4° C. for 2 months. Both curves practically overlap. The solution is storage stable as demonstrated by the virtual absence of a peak at a retention time of 30.5 min. in the grey overlay graph which would demonstrate the presence of acid sophorolipid, derived from hydrolyzed lactones.

Figure 5:
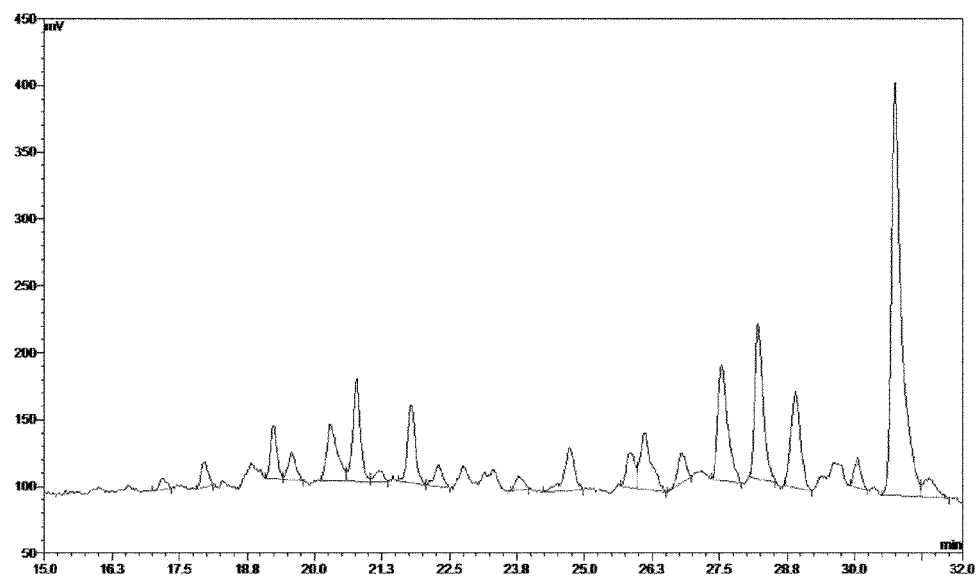
FIG. 5 is a graphic representation of a chromatogram recorded for the experiment described in Example 13. The chromatogram was recorded on a mixture of water-soluble sophorolipids, saturated with lactonic sophorolipids.
Figure 9:
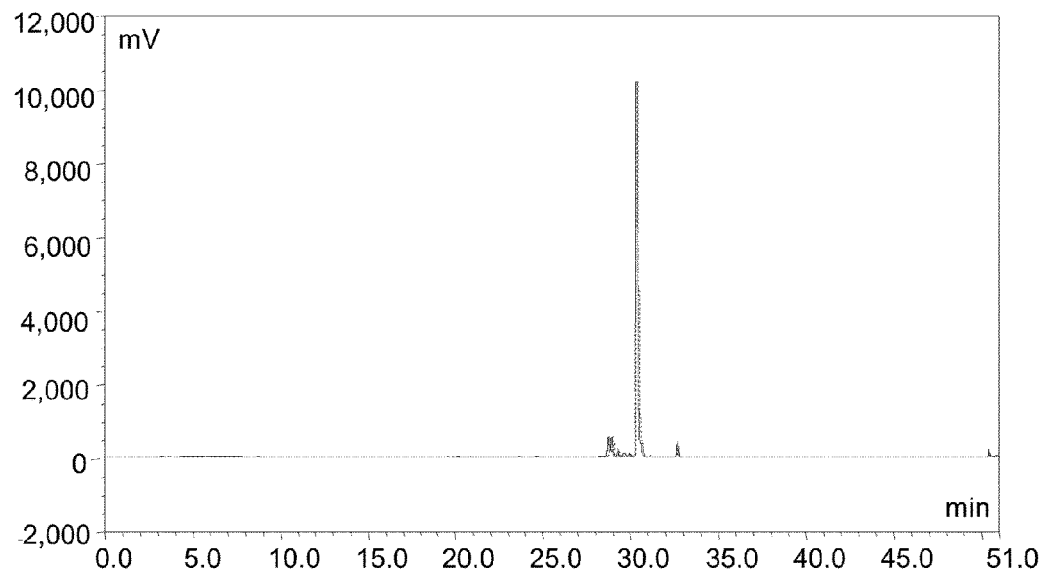

FIG. 9 is graphic representation of a chromatogram recorded on the same sample as for FIG. 5, after 2 months of storage at 40° C. Both curves practically overlap. The solution is storage stable as demonstrated by the virtual absence of a peak at a retention time of 30.5 min. in the grey overlay graph which would demonstrate the presence of acid sophorolipid, derived from hydrolyzed lactones.

DETAILED DESCRIPTION OF THE INVENTION

The present invention concerns an improved method for producing sophorolactone, sophorolactone in solid form obtained with an improved degree of purity and uses for this sophorolactone. The access to sophorolactone provided by the invention further allows improvements in the production of sophorolactone derivatives. The invention provides a method for producing at least partially hydrolysed sophorolactone, ω and ω-1 hydroxy fatty acids and sophorose derived from sophorolactone.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein. The recitation of numerical ranges by endpoints includes all numbers and fractions subsumed within that range, as well as the recited endpoints.

The present invention provides an improved fermentation process for the production of sophorolipids in lactone form, also called sophorolactones. Within the scope of the present application sophorolipid refers to the non-acetylated sophorolipid as well as to its acetylated derivative.

For the fermentation use is made of a *Candida* species capable of producing sophorolactone. *Candida* species which are particularly preferred for sophorolipid production according to an embodiment of the invention are *Candida bombicola* and/or *Candida apicola*; most preferably *Candida bombicola*.

In a preferred embodiment of a process according to the invention, the process is split-up over a step wherein *Candida* species are cultivated in the absence of an oil or oily substrate. This step will be named the pre-cultivation. By the term "pre-culture" it is meant herein, the stage of the synthesis process preceding the fermentation steps. This preculture stage yields the required *Candida* biomass for appropriate inoculation of the full fermentation volume.

Growth of micro-organisms can be displayed in a biomass growth curve. It typically displays a part of exponential growth, the so-called log phase or phase of exponential growth, followed by a stationary phase, in which the size of a population of microorganisms remains constant, even though some cells continue to divide and others begin to die. As the population grows, microorganisms consume nutrients and produce waste products. When the nutrient supply is depleted, the growth rate enters a stationary phase in which the number of viable cells remain the same.

In the present invention, cells of the selected *Candida* species are pre-cultivated until a stationary growth phase is obtained. This deviates from the prior art wherein a preculture is typically obtained from cell growth up to the stage of experimental growth. The inventors found that a pre-culture of cells grown until the stationary growth phase was reached was advantageous to increase sophorolactone yield.

The pre-cultivated cells thus obtained are then used in a culture wherein the pre-cultivated cells are brought in contact with at least one fermentable sugar and at least one fermentable substrate. The cells are provided with adequate supply of sugar and substrate.

By the term "fermentable sugar" it is meant herein, carbohydrates that can be assimilated by the *Candida* species. Suitable sugars for use in the invention are glucose, sucrose and raffinose. In a preferred embodiment, the sugar is glucose either in solid or in liquid form and glucose levels are maintained in excess of 20 g/l by intermittent glucose addition.

By the term "fermentable substrate" it is meant herein substrates that can be converted into sophorolipids, either by direct glycosidic coupling of a glucose unit to the (hydroxylated) substrate as such or by glycosidation after biochemical transformation of the substrate (e.g. hydroxylation) by the *Candida* species. The monoglycoside is subsequently converted into a sophorolipid by coupling to a second glucose unit. Suitable substrates for use in the invention are alkanes, fatty alcohols, fatty acids and their esters, including triglycerides and shielded esters. These substrates can be linear or branched, saturated, mono- or polyunsaturated with a carbon chain of 5 to 18 carbon atoms, preferably 12 to 18 carbon atoms, more preferably 15 to 18 carbon atoms.

In a preferred embodiment of a process according to the invention, the substrate is a triglyceride; preferably a triglyceride of saturated or unsaturated fatty acids with 16 or 18 carbon atoms; more preferably a vegetable oil; most preferably rapeseed oil.

In a preferred embodiment of a process according to the invention, the substrate is isostearic acid or isostearic alcohol, preferably isostearyl alcohol.

Fermentation takes place in an aqueous medium. Moreover, the addition of an organic solvent to harvest the sophorolactone is not required. The production and isolation of sophorolactone may be executed in aqueous media, without organic solvents.

In a preferred embodiment of a process according to the invention, use is made of a hydrophobic hydrocarbon substrate which corresponds to a shielded ester. Within the scope of the present invention, a shielded ester designates a compound represented by formula III, or a salt or a methyl, ethyl or glycerol ester of the compound of formula III which contains at least one cleavable bond,

$R^{10}-R^1-X-Y-Z-R^2-R^{20}$ (formula III)

and wherein
- —Y is —O—, —S—, —NH—, a mono or di unsaturated bond,
- X and Z may be the same or different and are chosen from the group of a —CO— group or a —CH$_n$(CH$_2$)$_m$— group which may be straight or branched, with m having a value between 0 and 4 and n between 0 and 2,
- $R^1$ and $R^2$ each are aliphatic hydrocarbon chains which may be the same or different chain, which may be branched or unbranched, may contain one of more unsaturated bonds and may contain one or more substituents,
- $R^{10}$ and $R^{20}$ may be the same or different and are chosen from the group of —H, —CH$_3$, —CHO, —CH$_2$OH, —COOH, —CHS, —CH$_2$SH, —CN or —CH$_2$NR$^3_p$, $R^3$ being an aliphatic hydrocarbon chain or H, p being 1 or 2,
- $R^{10}-R^1-X$ is a lipophilic moiety of the glycolipid,
- —Z—$R^2$—$R^{20}$ is an elongator part of the compound of formula III, wherein the number of atoms in the chain determining the chain length of formula III is between 14 and 22, preferably between 16 and 18 and in that the at least one cleavable bond is broken to remove the elongator part from the glycolipid to obtain a short chained glycolipid.

In a preferred embodiment, the compound of formula III is a so called shielded ester, wherein the hydrocarbon chain which determines the chain length of each of $R^{10}-R^1-X-$ and —Y—Z—$R^2$—$R^{20}$ contains at least 3 carbon atoms. The $R^{10}-R^1-$ and/or —$R^2$—$R^{20}$ part of the shielded ester may contain unsaturated carbon-carbon bonds. Within the scope of the present invention, a shielded ester designates a compound represented by formula III, wherein the functional group —X—Y—Z— is spaced apart from the end part of formula I by 3 or more carbon atoms.

Such shielded, cleavable esters may be synthesised chemically or enzymatically using methods well known to the person skilled in the art. In this shielded ester the functional group —X—Y—Z— is sufficiently far away from the terminal part of the molecule, so that its accessibility to extra-cellular enzymes is minimal. Although the use of conventional terminal esters—i.e. methyl-, ethyl-esters and glycerides—as substrates for sophorolipid synthesis has been well documented, these esters are readily hydrolysed by extracellular enzymes into C16-18 carboxylic acids. Terminal esters will mainly yield C18 sophorolipids, which can be converted into shorter chained sophorolipids in case they contain one or more unsaturated carbon-carbon bonds. This can for instance be achieved by subjecting the C18 sophorolipid to ozonolysis, removing any salts and dicarboxylic acids and obtaining sophorolipids with a chain length of 9 carbon atoms; as is described in EP1953237. Examples of shielded esters suitable for use in the present invention are provided in Table 1 below. n is the number of carbon atoms in the chain length determining part of the alcohol and m the number or carbon atoms in the chain length determining part of the carboxylic acid minus two.

In a preferred embodiment of a process according to the invention, the substrate is a shielded ester of formula H—(CH$_2$)$_n$—O—CO—(CH$_2$)$_m$—COOH with an apparent chain length of 16 to 18, i.e. with 15 to 17 carbon atoms.

In a preferred embodiment of a process according to the invention, the substrate comprises a carbon chain length lower than C14, preferably between C8 and C14, and the fermentation medium comprises cells of a *Candida* species modified to improve the conversion of said substrate with short carbon chain length into sophorolactone. Such species are for instance the *Candida bombicola* mutant strain M18, M30 or M33; preferably *Candida bombicola* M30. Use of these modified species has for effect that the sophorolactones will be produced with a corresponding chain length in their fatty acid moiety at an improved yield. Yield will be improved as these species have been genetically modified so that the beta-oxidation pathway is blocked. As a consequence, a side reaction wherein a substrate comprising a carbon chain length below C14 is metabolized rather than converted into a sophorolipid is blocked.

In a preferred embodiment the pre-cultivated cells are fermented in a fed-batch set-up. The sugar and substrate are fed to the pre-cultivated cells in fed batch mode. Use of a fed-batch fermentation as production technique has the advantage that the nutritional environment required for fermentation can be kept approximately constant during the course of the batch. The production of by-products that are generally related to the presence of high concentrations of substrate can be avoided by limiting its quantity to the amounts that are required solely for the production of the sophorolipid.

Cultivation of the pre-cultivated cells takes place in conditions such that the cells metabolize the sugar and substrate to sophorolipids. In a preferred embodiment of a process according to the invention, the substrate comprises corn steep liquor or CSL. Corn steep liquor is known as a source of lactic acid. It is a commercially available product. It is a viscous yellowish or dens brown liquid or powder obtained by concentration of corn steep water. The dry matter content is usually 45-55%, preferably 48-52%. The pH is in the range of 3-5, preferably 3.5-4.5. The protein content (Dry Matter) is typically 30-50%, preferably 35-45%. In a preferred embodiment of the method, the growth medium comprises 50-60 g/l glucose.H2O, 3-8 g/l corn steep liquor, 2-6 g/l $(NH_4)_2SO_4$, 0.5-1.5 g/l $KH_2PO_4$, and 0.1-1.0 g/l $MgSO_4.7H_2O$. In a preferred embodiment the corn steep liquor is in the form of a powder.

TABLE 1

Examples of preferred shielded esters of formula
H—$(CH_2)_n$—O—CO—$(CH_2)_m$—COOH

| n | monoAlcohol | m | diAcid | Total* |
|---|---|---|---|---|
| 8 | 1-octanol | 5 | Pimelic | 16 |
| 8 | 1-octanol | 6 | Suberic | 17 |
| 8 | 1-octanol | 7 | Azelaic | 18 |
| 9 | 1-nonanol | 4 | Adipic | 16 |
| 9 | 1-nonanol | 5 | Pimelic | 17 |
| 9 | 1-nonanol | 6 | Suberic | 18 |
| 10 | 1-decanol | 3 | Glutaric | 16 |
| 10 | 1-decanol | 4 | Adipic | 17 |
| 10 | 1-decanol | 5 | Pimelic | 18 |
| 11 | 1-undecanol | 2 | Succinic | 16 |
| 11 | 1-undecanol | 3 | Glutaric | 17 |
| 11 | 1-undecanol | 4 | Adipic | 18 |
| 12 | 1-dodecanol | 1 | Malonic | 16 |
| 12 | 1-dodecanol | 2 | Succinic | 17 |
| 12 | 1-dodecanol | 3 | Glutaric | 18 |
| 13 | 1-tridecanol | 0 | Oxalic | 16 |
| 13 | 1-tridecanol | 1 | Malonic | 17 |
| 13 | 1-tridecanol | 2 | Succinic | 18 |
| 14 | 1-tetradecanol | 0 | Oxalic | 17 |
| 14 | 1-tetradecanol | 1 | Malonic | 18 |
| 15 | 1-pentadecanol | 0 | Oxalic | 18 |

*the total length of the resultant ester as compared to a normal, linear fatty acid The conditions comprise selection of a suitable temperature and suitable oxygen supply. A suitable temperature is in the range of 24° C.-30° C., more preferably about 25° C. Suitable oxygen supply can be pure oxygen, oxygen enriched air or preferably air, the latter introduced in the fermenter at an aeration rate from 0.05-1.5 vvm, preferably starting at 0.5-1 vvm and reducing the aeration in case of risk for overfoaming to 0.05-0.5 vvm.

Under the fermentation conditions a sophorolipid composition is produced comprising sophorolipids in acid form and sophorolipids in lactone form.

Furthermore fatty acid will be formed in the reaction mixture.

The inventors have found that it is particularly advantageous to suppress the formation of excess fatty acid in the reaction mixture so that it does not reach more than 10 g/l.

In a preferred embodiment of a process according to the invention, the fatty acid levels are suppressed by adjusting the level of substrate fed to the metabolizing cells. For example, on the first day after inoculation, starting immediately after inoculation 0.5 g/l·h of oil is added, after that 1.5 g/l·h of oil is added unless the fatty acid level becomes too high.

In a preferred embodiment of a process according to the invention, the fatty acid level of the reaction mixture is suppressed below 10 g/l, preferably below 8 g/l, more preferably between 1-5 g/l, expressed in weight of acid per liter of reaction mixture.

Suppression of the fatty acid level has for effect that the resulting mixture of sophorolipids formed is less complex. It has the advantage that conditions for the crystallization of sophorolactone are created. Access to this compound in solid form, allows the lactone and acid form to be separated without the use of organic solvents. It has the further advantage of yielding very low levels of residual fatty acid in the sophorolactone composition.

Formation of fatty acid in the reaction mixture must be suppressed below a predetermined level such that at least part of the sophorolactone produced will become available in the form of crystals.

It was found that when a bioconversion process finished and the decanted sophorolactone phase contained in excess of 2% free fatty acids, expressed in weight on the weight of the total dry matter that the solidification of said phase does not occur. Because the raw material stays liquid, it is not possible to extract purified lactone out of it without resorting to an economically far less interesting process involving organic solvents instead of using just water.

Another drawback to an excess amount of free fatty acids entails the decanted sophorolipids having an increased water content, which also reduces the overall economics of the process as this will increase transportation cost.

Upon production of a sufficiently high yield of the desired compounds, the reaction mixture is warmed to a temperature between 60° C. and 90° C., preferably 70° C., thereby melting the sophorolactone crystals. The molten sophorolactone is allowed to settle to the bottom of the fermenter. A lower layer will form providing a crude sophorolactone composition. The crude sophorolactone composition can be removed from the remainder of the reaction mixture without difficulties. The addition of an organic solvent, e.g. to extract the sophorolactone from the mixture, is not required. This is advantageous as it avoids that the resulting sophorolactone is contaminated with traces of organic solvent. Because of the high temperatures and exposure time this process will have the effect of pasteurization. This results in killing off the yeast cells thus facilitating disposal of the broth remaining after product extraction. The filtration step removes cell debris from the sophorolactone composition.

In a preferred embodiment of a process according to the invention the process comprises the following purification procedure. This procedure can be carried out on the crude sophorolactone composition which has settled to the bottom of the fermenter. It can also be carried out on a crude sophorolactone composition which has been removed from the fermenter.

The crude sophorolactone composition is cooled to a temperature whereby the sophorolactone solidifies. The composition is cooled preferably until a paste is formed. If the paste is still in the fermenter it is drained from the fermenter. For example, by opening the fermenter at the bottom and draining the crude sophorolactone composition from the fermenter. Alternatively the supernatant broth is removed and the paste is allowed to be formed in the fermenter. Formation of a paste can be improved by seeding with a dry lactone powder material from a previous production.

In a preferred embodiment, the solid, such as a paste, is dispersed in water at a temperature of 5-25° C., preferably 10-15° C.; more preferably at 10° C.

The mass ratio of water to solid is preferably between 0.5 and 15. The use of this amount of water assures that sophorolipids present in the acid form dissolve well in contrast to the sophorolipids present in lactone form. These are poorly water soluble. The poor water solubility is even worsened by the temperature of the water. The sophorolactone present crystallizes and an aqueous dispersion of sophorolactone results.

In a preferred embodiment decalcified water is used. Calcium ions present in the water would otherwise form calcium salts with the sophorolipids present in acid form. The formation of calcium salts is undesirable because it hampers the valorization of sophorolipids other than the sophorolactones.

In a next step, the sophorolactone is separated from the water; e.g. by decantation or centrifugation. This has for effect that the sophorolipids present in the dispersion are fractionated. The acid form remains in the water, whereas the sophorolipids in lactone form, i.e. sophorolactone, is separated off, in the form of crystals.

The procedure of dispersing and separating may be optionally repeated. Preferably the steps are repeated 0 to 10 times. In a preferred embodiment, the temperature of the water is kept below 40° C., preferably below 30° C. during the procedure. This has for effect that the crystals are not molten. Keeping the sophorolactones in crystal form has the advantage that optimum separation between the acid and lactone form results and the amount of water in the sophorolactone is reduced to a minimum.

In a preferred embodiment of a process according to the invention, the crude sophorolactone composition is brought to a temperature between 35° C. and 55° C. to melt the sophorolactone crystals present, thereby providing a lower layer comprising sophorolactone and an upper layer of supernatant water; separating the lower layer from the upper layer to obtain a composition with increased sophorolipid content versus the crude sophorolactone composition.

The resulting sophorolactone composition, i.e. paste or crystals, are dried. The crystals can be dried initially by centrifugation. Additional drying techniques can be used to dry the crystals further. The purification and drying step results in a sophorolactone in solid form. In a preferred embodiment the drying is by spray drying, drum drying, convection drying, thin film evaporation, vacuum drying, flaking, extruding or casting.

The resulting supernatant water fraction is preferably recycled. In purifying sophorolipid lactone by washing sophorolipids after bioconversion repeatedly with water, the first volume of wash water contains sufficient active matter for it to be used economically. In addition, subsequent washing steps are necessary to obtain a white end product. This will yield wash water with lower amounts of sophorolipids than in a preceding wash step, which would be regarded as waste.

In order to minimize waste and maximize the amount of recovered sophorolipids, it is possible to utilize the wash water obtained from a subsequent step for creating the suspension in which the lactone is being washed. Preferably, five of subsequent washing steps are performed. The wash water from steps 2 through 5 can be stored until they can be used in a subsequent washing sequence. Step 1 provides a washing slurry from the raw sophorolipids (i.e. the bioconversion product) and the wash water obtained from step 2 (as stored from a previous purification run). This slurry is then separated into semi-washed lactone and wash water rich in sophorolactone. The semi-washed lactone is then suspended again, this being step 2, in wash water from a previous step 3 and so forth. Step 5 does not use wash water, but fresh water instead. Preferably two volumes of wash water are used for each volume of raw sophorolipids. Thus the washing water travels from the end of the sequence back to the front, accumulating the water soluble components, and the insoluble lactone travels in the opposite direction.

The resulting process results in a counter current purification of the sophorolactone with reduced amounts of waste and fresh water requirements. Due to the selectivity of a process according to an embodiment of the invention, problems with foam and the need for foam suppression are reduced.

During the settling of a crude sophorolactone composition in the fermenter, small amounts of yeast and cell fragments from the micro-organism may become entrapped in the drained precipitate. After settling a border layer of yeast cells on top of the warm sophorolipids is formed. Part of this layer may also be drained along with the sophorolipids, both sources resulting in small amounts of particulates in the products. The inventors were able to solve the problem of entrapped material by the use of depth filtration.

In a preferred embodiment of a process according to the invention, the process additionally comprising the step of filtering the sophorolactone separated off the reaction mixture by depth filtration. In a more preferred embodiment depth filtration is carried out at a temperature between 40° C. and 90° C. and a pressure of between 0.5 bar and 2.5 bar. Most preferably depth filtration is carried out at a temperature between 60° C. and 70° C. and a pressure between 0.5 and 2.0 bar.

In a preferred embodiment of a process according to the invention, the sophorolactone separated composition off the reaction mixture is in the form of an aqueous sophorolipid mixture comprising at least 30 wt %, preferably at least 70 wt %; more preferably at least 80 wt % sophorolactone, expressed on the dry matter content of the aqueous sophorolipid mixture.

In a preferred embodiment of a process according to the invention, the sophorolactone is comprised in a composition comprising at most 60 weight percent water; preferably at most 50 weight percent water; most preferably at most 40 weight percent water.

In a preferred embodiment of a process according to the invention, the fermentation is executed in a vessel at an overpressure of between 0-1.5 bar, preferably at 0.5-0.6 bar. This has the advantageous that foam formation can be suppressed.

In a further aspect the present invention provides a sophorolactone composition in the form of a solid or paste, obtainable by a method according to an embodiment of the invention, consisting of 15-70 wt % sophorolactone, preferably 30-70 wt %; 0-30 wt % sophorolipid acid, preferably 0-15 wt %; 0-1 wt % fatty acid, preferably 0-0.5 wt %, and remainder water.

In a preferred embodiment the sophorolactone composition obtainable by a method according to the invention comprises at least 60 weight percent sophorolactone and at most 40 weight percent water.

In a preferred embodiment the sophorolactone composition consists of 70-100 wt % sophorolipid lactone, 0-1 wt % sophorolipid acid, preferably 0-0.5%, less than 0.1 fatty acid, and remainder water. In a more preferred embodiment the sophorolactone composition consists of at least 95 wt %, more preferably at least 98 wt %, most preferably at least 99 wt % sophorolactone.

Due to its limited solubility in water and solvents such as ethanol, access to some applications is limited. The inventors have found a range of solvents which display an improved solubility of sophorolactone over water and ethanol. Moreover, the dried sophorolactone resulting from a method of the invention, which is essentially free of water, can advantageously be combined with these solvents to provide a storage stable sophorolactone composition.

In a third embodiment, the present invention provides a formulation obtained by dissolving the sophorolactone composition in a solvent which dissolves sophorolactone particularly well.

noxyethanol, benzylalcohol, methanol, isopropanol, phenetyl alcohol, glycerin formal, ethylacetate, DPM, PNP, PNB, ethyllactate, isoamyl lactate, butyl lactate, glacial acetic, D-limonene, hexanol, dimethyl lactamide, DMI, glycerincarbonate, 2-3-o-isopropyliden glycerin, hydrocinnamylalcohol. Of these solvents the following were able to dissolve sophorolactone in excess of 15%: phenoxyethanol, benzylalcohol, phenetyl alcohol, glycerin formal, DPM, PNP, ethyllactate, isoamyl lactate, butyl lactate, dimethyl lactamide, DMI, 2-3-o-isopropyliden glycerin, hydrocinnamylalcohol. And the following solvents were able to dissolve sophorolactone in excess of 30%, the exact amount specified in brackets (also featuring in FIG. 1): phenoxyethanol (36%), benzylalcohol (67%), glycerin formal (35%), dimethyl lactamide (66%), DMI (32%), 2-3-O-isopropyliden glycerin (36%), hydrocinnamylalcohol (33%).

TABLE 2

Hansen Solubility Parameters for a selected range of solvents together with their capacity to dissolve sophorolactone; δD, δP and δH respectively stand for the dispersion parameter, polar parameter and hydrogen bonding parameter. They are expressed in $MPa^{1/2}$.

| Solvent | CAS n° | δD | δP | δH | % lactone dissolved | GRAS status |
|---|---|---|---|---|---|---|
| Water | 7732-18-5 | 15.5 | 16 | 42.3 | <1 | OK |
| Glycerol | 56-81-5 | 17.4 | 12.1 | 29.3 | <1 | |
| 1.3 propanediol | 504-63-2 | 16.8 | 13.5 | 23.2 | 2.75 | |
| Propylene glycol | 57-55-6 | 16.8 | 9.4 | 23.3 | 9.05 | |
| Caprylyl Glycol | 1117-86-8 | | 6.3 | 15.5 | 8.65 | |
| Ethanol | 64-17-5 | 15.8 | 8.8 | 19.4 | 7.5 | |
| Phenoxyethanol | 122-99-6 | 17.8 | 5.7 | 14.3 | 35.53 | NOK |
| Benzylalcohol | 100-51-6 | 18.4 | 6.3 | 13.7 | 67.35 | OK |
| Methanol | 67-56-1 | 15.1 | 12.3 | 22.3 | 8 | |
| Isopropanol | 67-63-5 | 15.8 | 6.1 | 16.4 | 2.2 | |
| Phenetyl alcohol | 60-12-8 | 19 | 5.8 | 12.8 | 22 | OK |
| Glycerin formal | 5464-28-8 | 16.37 | 11.99 | 19.63 | 35 | NOK |
| Ethylacetate | 141-78-6 | 15.8 | 5.3 | 7.2 | 3.96 | |
| Glacial acetic | 64-19-7 | 14.5 | 8 | 13.5 | 23.65 | |
| Diethylether | 60-29-7 | 14.5 | 2.9 | 5.1 | | |
| DPM | 34590-94-8 | 15.5 | 5.7 | 11.2 | 28.93 | NOK |
| PNP | 1569-01-3 | 15.8 | 7 | 9.2 | 15.57 | |
| PNB Henkel | 005131-66-8 | 15.3 | 4.5 | 9.2 | 6.73 | |
| Ethyllactate | 141-78-6 | 16 | 7.6 | 12.5 | 19.45 | OK |
| Isoamyl lactate | 19329-89-6 | 15.5 | 5.4 | 12.3 | 21.2 | NOK |
| D-limonene | 5989-27-5 | 13.2 | 1 | 4.7 | 8.5 | |
| Butyl lactate | 138-22-7 | 15.8 | 6.5 | 10.2 | 20 | OK |
| Hexanol | 111-27-3 | 15.9 | 5.8 | 12.5 | 2.65 | |
| Dimethyl lactamide | 35123-06-9 | | | | 65.64 | NOK |
| Dimethyl isosorbide | 5306-85-4 | 17.18 | 9 | 8.18 | 31.89 | NOK |
| Glycerincarbonate | 931-40-8 | 17.9 | 9.6 | 18.9 | <1 | |
| 2-3-o-isopropyliden glycerin | 100-79-8 | | | | 36.18 | NOK |
| Hydrocinnamylalcohol | 122-97-4 | 18.6 | 5.6 | 12.7 | 32.5 | OK |

Figure 1:
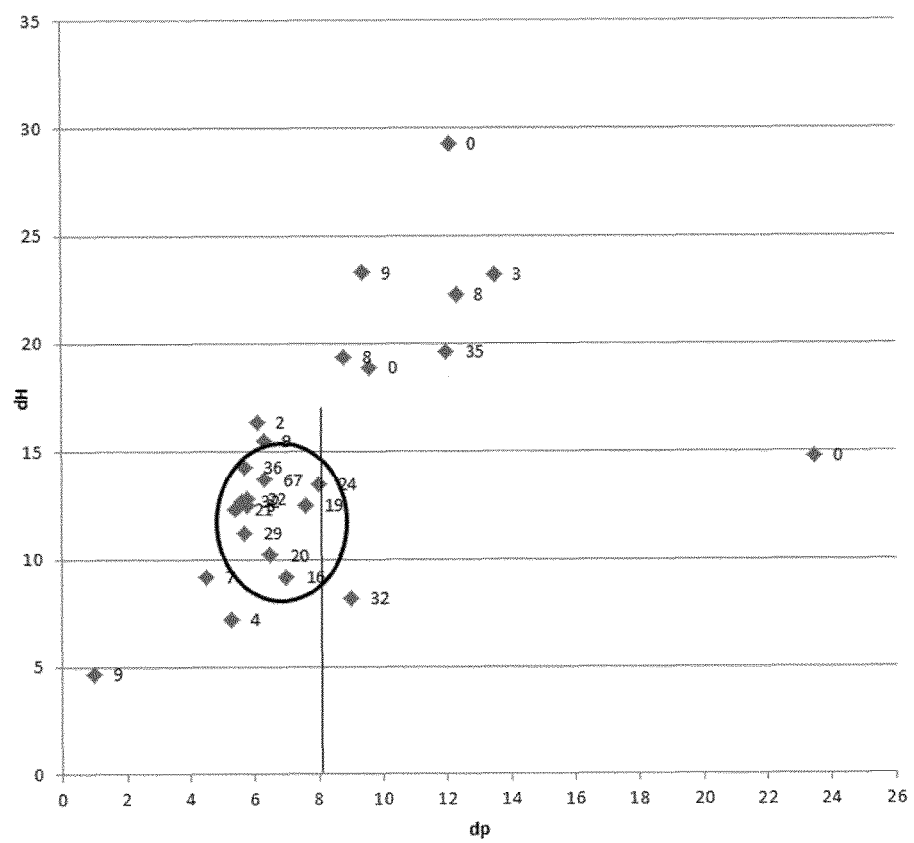

The inventors have found a range of solvents that are particularly suitable for dissolving sophorolactones. These solvents have in common that they can be characterized by similar Hansen Solubility Parameters. Each solvent investigated was given three Hansen parameters, each measured in MPa: delta D characterizing the energy from dispersion bonds between molecules, delta P characterizing the energy from dipolar intermolecular forces between molecules and delta H characterizing the energy from hydrogen bonds between molecules. The results are summarized in a graph in FIG. 1 and in Table 2. In FIG. 1, the datapoint numbers representing the percent sophorolactone dissolved at room temperature by the solvents with the particular delta P-delta H combination. The 27 solvents tested in the experiment and depicted in the Figure are as follows: water, glycerol, 1.3 propanediol, propylene glycol, caprylyl glycol, ethanol, phe- Solvents characterized by a delta P between 5 and 9.5 and a hydrogen bonding parameter between 8 and 15, were found to be particularly suitable as solvent for sophorolactone. In a preferred embodiment, the solvent in a formulation according to an embodiment of the invention is selected from the list of phenoxyethanol, benzylalcohol, phenetyl alcohol, hydrocinnamylalcohol, tetrahydrofurfuryl alcohol, dimethylisosorbide, methyl salicylate eugenol, linalool, hexanol, glacial acetic, dimethylcarbonate, certain glycolethers such as dipropyleneglycol methyl ether and 1-propoxy 2-propanol and lactate esters including ethyl-, butyl-, amyl-, ethylhexyl-lactate.

In a more preferred embodiment, the solvent in a formulation according to an embodiment of the invention has a dispersion parameter in excess of 17 $(MPa)^{1/2}$. Such solvents include for example phenoxyethanol, benzylalcohol, phenetyl alcohol, hydrocinnamylalcohol, tetrahydrofurfuryl alcohol, dimethylisosorbide, methyl salicylate and eugenol.

The method of the invention provides an economically interesting access to sophorolactone with improved purity. In turn, this opens up new possibilities. In particular, a method according to an embodiment of the invention provides sophorolactone in dry form. The virtual absence of water makes it possible to use it as auxiliary in formulations with alkaline pH, such as alkaline washing powders and washing tablets. In the presence of water, the sophorolactone hydrolyzes to its acid form, causing the formulation to change its foaming behavior. Especially for automated dishwashing powders and tablets it is an advantage that the foaming behavior of the formulation remains stable. The application requires low foaming behavior. Increased foaming could lead to blockage of the automated dishwasher wherein these tablets or powders are used.

In a further aspect, the invention provides a dry solid product for laundry or dishwashing, comprising the sophorolactone composition consisting of 70-100 wt % sophorolactone, 0-1 wt % sophorolipid acid, preferably 0-0.5% sophorolipid acid, less than 0.1% fatty acid, and remainder water, wherein the pH of the product is 8.0-14.0, preferably 8.5-11.50, as measured on a 1% solution of the product in water.

In a fifth aspect the invention provides a process for the preparation of partially hydrolysed sophorolactone. As starting materials a sophorolactone obtained by a process according to the invention is used. At least part of the sophorolactone is hydrolysed.

For this purpose a base is added to the sophorolactone. Between 0.5 to 1 equivalents of base are used compared to the sophorolactone. Partially hydrolysed sophorolactone compositions thus obtained have the advantage that their high purity is maintained and at the same time the low water solubility of the formulation is improved by providing lactone in acid form which solubilizes the lacton. Preferably sophorolactone is partially hydrolyzed, providing a formulation whereby of the sophorolipids present 39-45% are in the acid form and 55%-61% are in the lactone form.

Alternatively hydrolysis of at least part of the sophorolactone is obtained by heating the sophorolactone. Preferably the sophorolactone is heated for more than 4 hours, more preferably for more than 24 hours. The sophorolactone is heated to a temperature between 70-90° C., preferably to a temperature between 80-90° C.

The treatment with a base or heating, results in sophorolipid lactone which is at least partly hydrolysed to sophorolipid acid and corresponding salt. The advantage of this method is that a composition with pre-determined foaming behavior can be obtained. Foaming behavior can be changed from non-foaming corresponding to a composition comprising 100% sophorolactone to a composition which is highly foaming comprising 100% hydrolysed sophorolactone or sophorolipid in acid form. As a sophorolactone was used that is substantially free of water, the resulting composition can also be obtained as substantially water free. Hence, an composition with improved hydrolytic stability is obtained. The foaming behavior remains stable during storage.

The invention further provides a method for the preparation of ω hydroxy fatty acids of formula CH2OH—CH2-(CH2)n-COOH (IV) or ω-1 hydroxy fatty acids of formula CH3-CHOH—(CH2)n-COOH (V). These acids are obtained by starting from a sophorolactone obtainable using a method according to an embodiment of the invention. The sophorolactone is hydrolysed to the corresponding diacetylated sophorolipid in acid form, preferably by hydrolysing the sophorolactone using a base. Optionally the sophorolipid obtained is submitted to ozonolysis, removing any salts and dicarboxylic acids in order to obtain sophorolipids with a chain length of 9 carbon atoms. The head and tail portion of the molecule are separated. Separation can be obtained by hydrolysis with a weak acid or by enzymatic reaction. This results in the sugar moiety of the molecule and the ω and ω-1 hydroxy fatty acid moiety. The sugar moiety and/or hydroxy fatty acid are recovered. Preferably both the sugar moiety and hydroxy fatty acid are recovered.

A sugar moiety corresponding to sophorose is of great economic value. It is a potent inducer of cellulase production e.g. by the fungal species *Trichoderma reesii*. Cellulases are widely used e.g. in laundry washing and textile seizing, and production of bioethanol from cellulosic material. However, thus far the access to an economically feasible and large-scale production process was very limited. The process of the invention provides access to a route which starts from sophorolactone with improved purity. This facilitates the access to a purer sophorose. As the sophorolactone production can be practised on a large scale, larger scale sophorose production becomes accessible. Sophorose obtained by a method according to the invention may be used as inducer of cellulase producing micro-organism e.g. *Trichoderma*. Sophorose may be used as inducer for the enzyme cellulase, preferably for use in the production of ethanol. The sophorose obtained by the method of the invention provides access to a lower cost carbon source for the fermentation of sugars by cellulase thereby providing a more interesting access route to bio-ethanol.

In a preferred embodiment sophorolipids are split into sophorose and hydroxyl fatty acids. In the prior art, sophorose is destroyed as a strong acid hydrolysis is used. However, sophorose valorization is advantageous. It is e.g. key for low cost synthesis of hydroxyl fatty acids from sophorolipids.

The ω and ω-1 hydroxy fatty acids obtained by a method according to the invention have the advantage that they are derived from a process wherein the level of fatty acids of formula ROH wherein R is an alkyl chain, was kept very low. The resulting ω and ω-1 hydroxy fatty acids are characterized by lower levels of non-hydroxylated fatty acids of than in prior art methods, in particular below 0.8%. This is advantageous as this impurity is known for its ability to terminated polymerization reactions. The process of the invention results in product which is better suitable for polymerization reactions due to the substantial absence of these polymerization reaction terminators. This makes the ω and ω-1 hydroxy fatty acids obtained from the process of the invention, particularly suitable for use in polymerization reactions, for instance for the manufacturing of plastics. The invention is further described by the following non-limiting examples which further illustrate the invention, and are not intended to, nor should they be interpreted to, limit the scope of the invention. It is supposed that the present invention is not restricted to any form of realization described previously and that some modifications can be added to the presented example of fabrication without reappraisal of the appended claims.

EXAMPLES

Example 1

A preculture of *Candida bombicola* ATCC 22144 was grown for 72 hours at 25° C. in 4 Erlenmeyers of 1 liter medium each with the composition as listed in Table 3.

TABLE 3

| Corn steep liquor medium (CSL) | |
| --- | --- |
| Component | Concentration (g/l) |
| Glucose•$H_2O$ | 55 g/l |
| Dried CSL (Roquette) | 5 g/l |
| $(NH_4)_2SO_4$ | 4 g/l |
| $KH_2PO_4$ | 1 g/l |
| $MgSO_4$•$7H_2O$ | 0.5 g/l |

Figure 2:
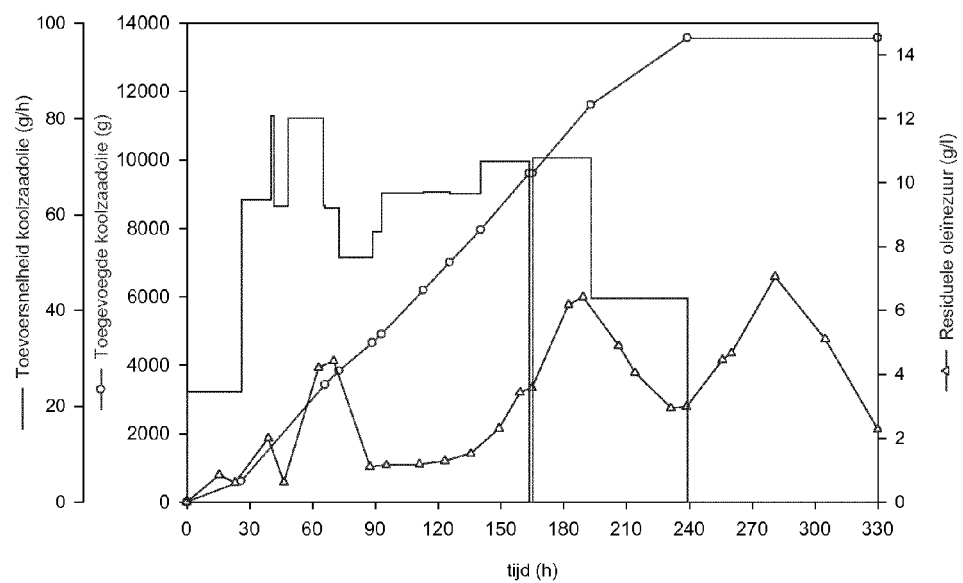

Contrary to prior art disclosures this preculture is essentially free of oily substrate and it was used in the stationary rather than in the exponential growth phase. After 72 hours the preculture is used to inoculate a previously sterilized Biostat U50 (Sartorius BBI Sytems) containing 40 liter sterile medium with the same composition as the preculture. A double fedbatch fermentation was operated at 110-130 rotations per minute (rpm), 25° C., 0.5 bar and pH 3.5. Aeration was set at 1 vvm (amount of the introduced air versus the bioreactor's working volume), decreased to 0.1 vvm after 40 hours in order to control excessive foam formation, and raised again after 180 hours to 1.3 vvm. Immediately after the inoculation 3.33 g/l rapeseed oil (Bioplanet, food grade) was added. After 24 hours the continuous feeding rate was set at 1 g/l·h. The feeding rate was controlled as a function of the residual oil and the residual oleic acid, targeting an oleic acid content of 1-5 g/l, at all times avoiding concentrations above 8 g/l. The feeding profile is illustrated in FIG. 2. The presence of residual oil in the fermentation broth was measured by taking a sample of fermentation broth, heating to 80° C., and by visual inspection observing if a layer of oil is formed.

Solid glucose was added as soon as the concentration dropped below 20 g/l. A linear increase of glycerol was observed from 0 g/l at 24 h to approximately 35 g/l at 264 h. This glycerol profile and the total disappearance of residual oil are considered to be good indicators for a correct fermentation. The most pronounced sophorolipid synthesis occurred during the first 160 hours of the fermentation during which 240 g/l of oil were added. Upon further addition sophorolipids were formed at a lower rate, with an increased risk of overdosing the oil and with a steep increase of broth viscosity. The sophorolipids were present as crystals during the fermentation as evidenced under the microscope (×100 magnification).

After 165 hours 299 g/l sophorolipids were formed, at a rate of 1.81 g/l·h and a substrate conversion of 0.71. At that point in time 5 g/l of residual oleic acid was present as measured with a hexane extraction. A HPLC-ELSD analysis was performed according to the method described by Steve Fleurackers in Eur. J. Lipid Sci. Techn., 108(1): 5-12, 2006. The analytical method described in this publication is herein incorporated by reference. This analysis revealed virtually no acid sophorolipids at 24.4 minutes retention time, the peak area of the lactone form being approximately 50 times that of the acid form. After 330 hours, 403 g/l sophorolipids were formed, at a rate of 1.22 g/l·h and a substrate conversion of 0.75. The residual oleic acid content had dropped to 2 g/l and the acid/lactone ratio remained stable with basically one HPLC peak.

The fermenter was then heated to 90° C. in order for the crystals to melt and to obtain an oily layer which after cooling is easily separated from the broth by draining the fermenter the next morning. Once stored in drums the sophorolipids readily crystallized again to take the shape of a hard solid.

Comparative Example 2

The experiment of Example 1 was repeated this time adding 5 g/l methyloleate (Cargill) to the preculture and continuously feeding methyloleate instead of rapeseed and feeding a total of 240 g/l to the fermenter. The ester feeding profile was again adapted to a maximum concentration of 5 g/l oleic acid. The preculture was grown for 24 hours at 25° C. It was in the exponential growth phase when used for seeding. A total sophorolipid yield of 262 g/l was obtained after 222 hours, with a production rate of 1.18 g/l·h and a substrate conversion of 0.58 (cf. Table 3). Several lactonic peaks as well as approximately twice the amount of acid sophorolipids are observed.

Comparative Example 3

The experiment of Example 2 was repeated with rapeseed instead of methyloleate. The preculture was grown for 30 hours at 25° C. and was in the exponential growth phase when used for seeding. The medium of both the preculture and the fermentation broth was made according to Lang et al (2000). Five gram per liter rapeseed oil (Bioplanet, food grade) were added to the seeded preculture.

A total of 240 g/l rapeseed was fed to the fermenter. A feeding profile was adapted targeting a maximum concentration of 5 g/l oleic acid. A total sophorolipid yield of 320 g/l was obtained after 240 hours, with a production rate of 1.33 g/l·h and a substrate conversion of 0.8 (cf. Table 2). An HPLC analysis revealed a clear peak at 24.4° indicating the presence of acid sophorolipids. These were probably the cause no crystallization occurred. Only upon storage for several weeks at 4° C. did gradual crystallization occur.

The results obtained from the experiments described in Examples 1-3 are summarized in Table 4. Comparing example 1 and 3, both using rapeseed oil as substrate and 1 versus 2 and 3 the latter working with a preculture in the exponential growth phase and containing oily substrate it is clear that using rapeseed oil as well as a medium based on corn steep liquor (CSL) results in a substantial increase of the production speed of sophorolipids. The sophorolipids obtained are in the crystalline form, which is important since this will allow isolation of lactone. The fermentation in Example 1 was seeded with a preculture in the stationary phase to which no oily substrate was added, confirming the hypothesis from many earlier experiments that this is beneficial for maximum yield of sophorolipids in the lactone form.

TABLE 4

Results obtained from the experiments described in Examples 1-3

| | Example 1 CSL-medium Rapeseed Stationary preculture | Example 2 CSL-medium Methyloleate exp. growth preculture | Example 3 Medium Lang et al Rapeseed exp. growth preculture |
| --- | --- | --- | --- |
| SL-yield | 299 g/L | 262 g/L | 319.5 g/L |
| Production rate | 1.81 g/L · h | 1.18 g/L · h | 1.33 g/L · h |
| Yield | 0.71 | 0.58 | 0.80 |
| Crystalline SL | Yes | No | No |

Example 4

Example 1 was repeated in a Biostat D100 containing 70 liter of CSL medium at 25° C. to which a total of 240 g/l rapeseed oil was added controlling the residual oleic acid content. The fermenter was inoculated using 1.4 liter CSL medium without oil and grown in 7 1-liter Erlenmeyers for 72 hours at 25° C. until the stationary phase was reached.

After 183 hours 254 g/l sophorolipids were present again virtually free of the acid form as evidenced under the microscope by the presence of crystals during the fermentation. The production rate and the substrate conversion were respectively 1.39 g/l·h and 0.62%.

Example 5

The previous example was repeated but using a preculture in the exponential growth phase (similar to example 3), grown with 5 g/l rapeseed oil for 25 hours at 25° C.

After 160 hours 246 g/l sophorolipids were present as an oily phase, probably due to the presence of substantial amounts of the acid form as evidenced by HPLC analysis. Continuing the fermentation process until 330 hours resulted in decreased production rate of 0.9 g/l·h and a total yield of 297 g/l.

Examples 4 and 5 confirm the importance of an oil-free preculture in the stationary phase for obtaining crystalline sophorolipids rich in the lactone form.

Example 6

Example 4 was repeated on a D100 fermenter feeding 240 g/l rapeseed oil in total to 70 liter of CSL medium, but this time working with 3 liter preculture cultivated in a Biostat B5 rather than Erlenmeyers. Four fermentations were set-up in the D100 varying the nature of the preculture.

The FB23 and FB35 precultures did not contain rapeseed oil, FB32 and FB34 contained 5 g/l rapeseed oil. The precultures were grown for a varying period of time until they reached a varying point of the stationary phase as summarized in Table 5 along with the results.

When adding rapeseed oil the stationary phase is reached approximately 24 h faster (data not shown). The best fermentation characteristics however are obtained when precultures are used without oil and from the moment they have reached the stationary phase. Using a more mature preculture is feasible as well.

Less acid sophorolipids were formed using a preculture without oil. Foam control was easier in FB23 and FB35 (no oil in preculture) compared to FB34 (oil in preculture). In the FB34 experiment stirring speed and aeration rate had to be lowered at about 48 hours until about 72 hours, in contrast to the other 3 experiments, to cut back on the foam. It is assumed that this is caused by the increased presence of acid sophorolipids.

Additional experiments (data not shown) were organized always yielding low amounts of acid sophorolipids (D100 FB22: 11%, D100 FB23: 15%, D100 FB24: 13%) when working with a stationary and oil free preculture.

TABLE 5

| | Experimental conditions and results | | | |
|---|---|---|---|---|
| | No oil Grown 48 h 0 h stationary FB23 | No oil Grown 72 h 24 h stationary FB35 | Oil Grown 48 h 24 h stationary FB34 | Oil Grown 72 h 48 h stationary FB32 |
| SL-yield | 265 g/L | 265 g/L | 248 g/L | 259 g/L |
| Production rate | 1.60 g/L · h | 1.45 g/L · h | 1.35 g/L · h | 1.39 g/L · h |
| Yield | 0.62 | 0.62 | 0.62 | 0.64 |
| Crystalline SL | Yes | Yes | Yes | Yes |
| Acid SL | 13% | 15% | 23% | 20% |

Example 7

A large scale production of sophorolipids was performed according to the method of the invention. A double fedbatch fermentation was performed in 3 stages:

| 1/Erlenmeyer Preculture: | 2 baffled Erlenmeyers → | 1 L culture |
| 2/Fermenter Preculture: | 150 L fermenter → | 100 L culture |
| 3/Main Fermentation: | 8 m³ fermenter → | 3.5 m³ to 5.25 m³ culture |

Preculture 1 consisted of 2 baffled Erlenmeyer flasks of 2 L with 0.5 L CSL medium as described in Example 1, but with only 55 g/l glucose rather than 110 g/l. After the sterilization, each Erlenmeyer was inoculated with 1 glycerol vial (2 mL in a Cryovial). The Erlenmeyers were shaken at 25° C. After 45 hours of growth, the culture reached the mid-exponential growth phase (Optical Density between 25 and 30). Inoculation in 100 L medium was carried out after 49 hours of growth.

Preculture 2 consisted of 100 L CSL medium as described in Example 1. Preculture 2 was grown in a 150 L fermenter. All media components were dissolved in decalcified water and before sterilization 10 mL of an antifoaming agent (Entschaeumer A 4050 HAC) was added. The pH of the medium was 5.7 which was not corrected for. All components were sterilized together for 35 minutes at 121° C. After sterilization, the pH reached a value of 5.4. After sterilization, the fermenter was inoculated with the Erlenmeyer preculture (two Erlenmeyer flasks with 0.5 L culture). At the moment of inoculation, the Erlenmeyer preculture had grown for 49 hours and reached an optical density of 21.8. The glucose in the Erlenmeyer Preculture was not depleted at that moment and the pH was approximately 3.

The Fermenter Preculture was grown at approximately 25° C., the temperature varied between 22 and 27° C. Oxygen limitation was avoided by fully opening the valve of the incoming air. An overpressure in the fermenter of 20 kPa was performed.

During fermentation, the pH decreased to pH 3.5 and was hereafter kept constant at this value by adding 0.5 N NaOH by a piston pump. The pH started to decrease after 10 hours and reached 3.5 after 25 h. The pH varied between pH 3.5 and pH 3.7 as a consequence of the unsecured adding of the NaOH. Approximately 15 L of 0.5M NaOH was added.

Most of NaOH was added during the first 48 hours of growth. Stationary growth phase was reached after 60 hours of fermentation.

The main fermentation was carried out in a 8 m$^3$ bioreactor with a working volume of 6.5 m$^3$. The fermentation started with a volume of 3.5 m$^3$ corn steep liquor (CSL) medium. Because the fedbatch adding of rapeseed oil has to start immediately after the inoculation, 1.75 kg rapeseed oil (amount for 1 hour) was added to the medium before sterilization. This gave time to install the pump for the feeding of the rapeseed oil and to connect all necessary tubings after the inoculation. So, fedbatch of the oil was started 1 hour after the inoculation.

All media components were dissolved in decalcified water. All components were sterilized together for 45 minutes at 121° C. This longer sterilization time was necessary to sterilize all death points in the fermenter. During the sterilization, the temperature increased slowly to 121° C. and also after the sterilization, the temperature decreases very slowly due to the low cooling capacity. The total sterilization time took about 8 hours. Because of this long heating up and cooling down period, together with the longer sterilization time (45 min), the medium became very brown due to Maillard reaction. The pH of the medium after sterilization and inoculation was 4.32.

The fermenter was inoculated with the fermenter preculture (100 L culture). At the moment of inoculation, the fermenter preculture was grown for 72 hours and reached an optical density of 51. The glucose in the preculture was not depleted at that moment (tested with glucose strips available from Roche) and the pH was approximately 3.5.

The fedbatch fermentation was performed at approximately 25° C., the temperature varied between 24 and 27° C. After 24 hours of fermentation, cooling became a problem because of the enlarged heat production of the culture (exponential growth phase). An extra cooling pump was switched on in order to keep the temperature at 25° C.

At the start of the fermentation, the airflow was set at 1.5 m$^3$/min. An overpressure in the fermenter of 500 kPa was performed. The agitation was approximately 75 rpm. Due to foam formation, which started after 36 hours of fermentation, the airflow had to be decreased several times in order to control the foam formation. The minimal air flow was 0.4 m$^3$/min. During fermentation, the pH decreased to 3.5 and was hereafter kept constant at this value by adding 10 N NaOH by means of a piston pump. The pH started to decrease after 4 hours and reached 3.5 after 11.5 h of fermentation. The pH varied between 3.4 and 3.9 as a consequence of the addition of the NaOH. Approximately 80 L of 10M NaOH were added. Most of NaOH was added during the first 48 hours of growth. During fermentation extra rapeseed oil and glucose were added.

Rapeseed oil was added non-sterile as a continuous flow. A total amount of 240 g/L (in relation to the starting volume) was added. This means a total volume of 916 L or 840 kg. The feeding rate of rapeseed was adjusted in function of the residual fatty acid content. This content was determined by extraction of a fermentation broth sample with hexane. This was done in such a manner as to not exceed a residual fatty acid content of 5 g/l and not to observe any residual oil on top of a heated sample after day 2. A total amount of 798 kg or 228 g/L of rapeseed oil, expressed in relation to the starting volume, was added to the culture.

Solid glucose was added discontinuously by opening the top plate after pressure release because there was a low risk for contamination during the fermentation. Addition was function of the actual glucose concentration in the culture, such that as soon as the concentration dropped below 20 g/l glucose was added. A total amount of 1250 kg glucose.H$_2$O was added during the fermentation.

The fermentation took approximately 216 hours (9 days). After 50 hours of fermentation, it was observed by microscope that the sophorolipids formed tubular micelles. As a consequence of this phenomenon, the sample became very viscous. After 65 hours of fermentation, the first crystals could be observed by microscopic observation of a sample of fermentation broth. Sophorolipids settled down after heating the sample. During the fermentation foam started to appear and the airflow had to be reduced. After 138 h, foam decreased and airflow was returned to normal. This foam decreasing is probably a consequence of the amount of the acid sophorolipids sinking below 20% of total sophorolipid content, the insoluble lactone cutting back on the foam. By HPLC-ELSD using a reversed phase C18 column, the amount of acid and lactone sophorolipids produced was determined. At the end of the fermentation, 13% of the sophorolipids were in the acid form, the vast majority occurred in the di-acetyl lactone form.

After 216 hours of fermentation, the whole culture was heated to 70° C. in order to melt all crystals. When a temperature of 70° C. was reached, agitation and aeration was interrupted in order to separate the sophorolipid phase and the aqueous phases. This was done overnight. Next morning, sophorolipids were collected from the bottom of the fermenter. It was necessary to steam the wall of the fermenter, because re-crystallization had occurred at the (cold) wall of the fermenter. Two barrels of 640 L and 9 barrels of 50 L were filled with sophorolipids. Only the last barrel contained impure sophorolipids mixed with yeast cells and cell fragments. The sophorolipid fraction drained from the fermenter was in the form of a paste.

Example 8

Figure 3:
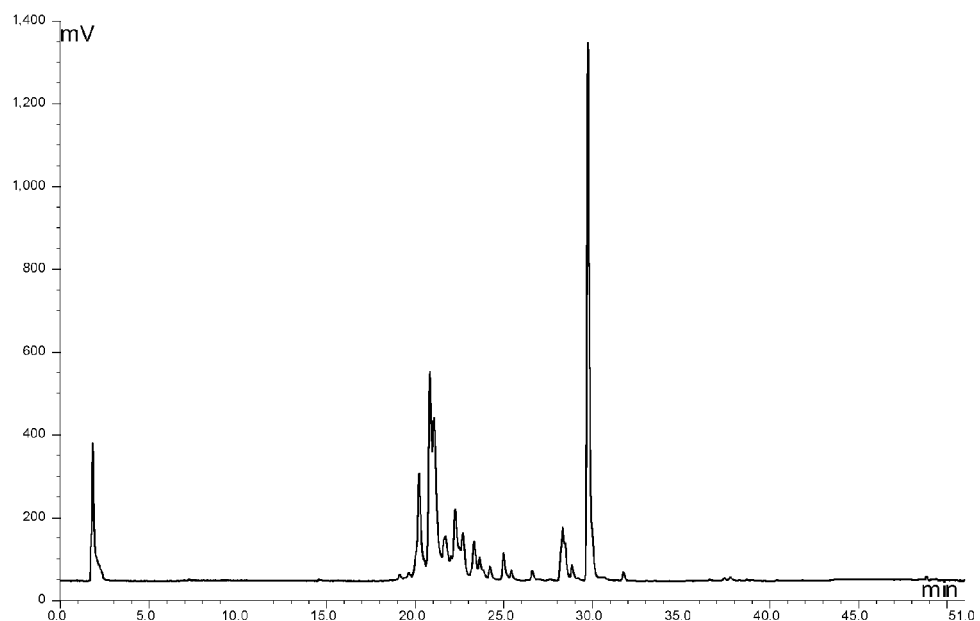
FIG. 3 is a graphic representation of a chromatogram recorded for the experiment described in Example 8 ($1^{st}$ wash, 1% in ethanol, 100 µl injection volume).

Sophorolipids were obtained as a liquid from the aforementioned fermentation of Example 7 through decantation. This dark brown liquid is allowed to solidify and will be referred to as "sophorolipid paste". It contained approximately 50% water and 0.1% cell fragments (visible as a haze when dissolving the paste in ethanol). The lactone form solidified at 30-35° C. resulting in a steep increase of the sophorolipid fraction. An amount of paste was dispersed in roughly the same weight of cold tap water to observe an almost immediate formation of an creamy opaque dispersion of soft white thin sharp lactone crystals of approximately 1-3 micron wide and 20-50 micron long with a crystal density of about 1.070 kg/l. The crystal phase accounted for approximately 30% of the dispersion volume. Further dilution with water lowered the viscosity of the suspension allowing the lactone to settle. This resulted after several hours in a clear brown watery supernatant. When dispersing the paste in an equal amount of water the first wash water contained approximately 20-25% dry matter with the HPLC profile as depicted in FIG. 3.

As evident from this chromatogram various sophorolipid forms are present in the wash water ranging from the most hydrophilic unacetylated acid form (elution time of ca. 20 min) to the most hydrophobic diacetylated lactone form (elution time of ca. 30 min). In addition a front peak (elution time ca. 2 min) is observed due to residual salts and sugars from the fermentation medium that were present in the 50-55% water of the crude sophorolactone composition.

Example 9

Figure 4:
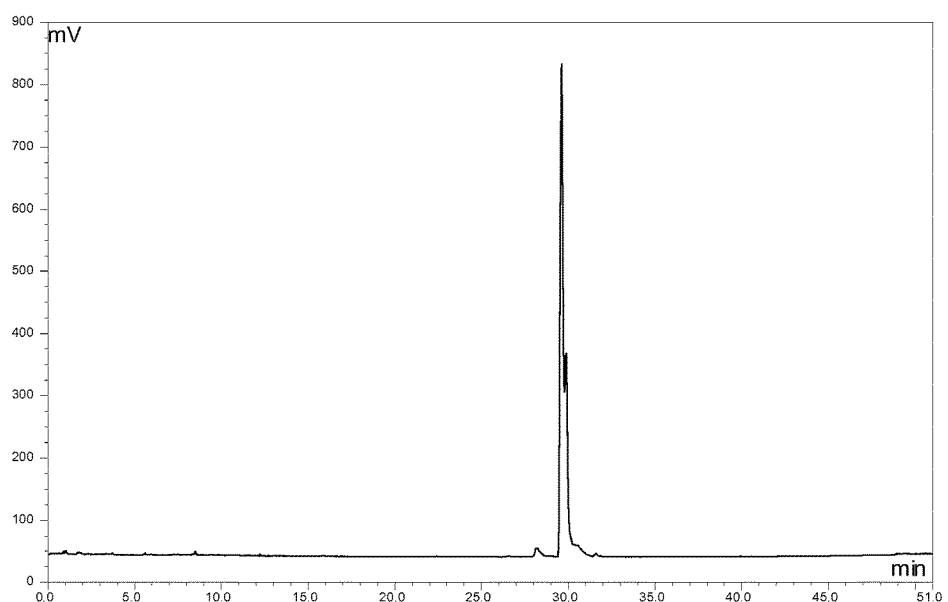
FIG. 4 is a graphic representation of a chromatogram recorded for the experiment described in Example 9 (sophorolactone with C18 carbon chain, 1% in tetrahydrofuran, 5 µl injection volume).

The previous Example 8 was repeated in 25 liter canisters. The lactone fraction was allowed to settle overnight. A clear supernatant was decanted. It was replaced with the same amount of fresh tap water, redispersed and again allowed to settle. The brown color gradually disappeared. After 10 cycles a pure white lactone fraction was obtained with the HPLC profile as depicted in FIG. 4.

Example 10

2200 g of sophorolipid paste from Example 7 was homogenized for 5 minutes in order to avoid undispersable lumps forming in the dispersion. The homogenized paste was dispersed in 4400 g of decalcified water through vigorous mixing, until a homogenous dispersion was obtained whilst cooling at 10° C. This dispersion had a liquid density of 1039 kg/l and a viscosity of 5.8 cP. A total of 6000 g of the initial dispersion was centrifuged (speed: 4000 rpm, radius: 190 mm, duration: 10 minutes). The supernatant was discarded and the remaining solid lactonic sophorolipids were again dispersed in 4760 g of fresh decalcified water, cooled to 10° C., to a total of 6000 g. Separation of the second dispersion was done in an identical manner. This process was repeated four times more, each time discarding the supernatant and replenishing the solid sophorolactones with fresh decalcified water cooled to 10° C. to a total of 6000 g, except for the sixth and final step where no fresh water was added. The resulting solid sophorolactones were visually inspected and found to have a white appearance. This colour is particularly suitable for use in applications where it is important to have uncoloured ingredients. This wet paste was left to dry under a stream of dry air for three days after which the resulting cake was converted into a white powder.

The use of a water-to-sophorolipid paste mass ratio below 0.5 was found to produce a dispersion which proved too viscous to readily separate the solid from the liquid phase. In several instances it was observed that, when uncooled water was used, the dispersion would convert from solid/liquid to liquid/liquid. The resulting heat from centrifugation and dispersion caused the dispersion to heat up to a point where the solid sophorolactones melted. These molten sophorolactones did not release appreciable amounts of impurities into the fresh wash water and as such, no further concentration, meaning purification, took place. The temperature at which this phase conversion of the sophorolactones occurs was determined to be at 49° C. This was established by gently heating a solid/liquid dispersion until a phase conversion was observed.

When liquid sophorolipids, either in the form of molten paste or in the form of sophorolipids dissolved in 2 parts of ethanol, were introduced into chilled water and the resulting dispersion was cooled as low as 5° C., no formation of dispersed solids was observed and a liquid/liquid dispersion maintained. It is assumed that the continuous mixing to maintain the dispersion interferes with the solidification of the sophorolactones needed in order to separate them. This instance demonstrates the necessity for letting the crude sophorolactone composition solidify before applying forces needed to bring them into a dispersion.

Example 11

Example 10 was repeated, with a total of five cycles of adding water to a paste of sophorolactones, mixing to obtain a dispersion and subsequently removing the bulk of the watery phase through centrifugation. To that purpose 1190 gram of sophorolipid paste was dispersed in 1800 gram of cold water. The lactone fraction was collected after centrifugation and decantation. All five liquid phases which were removed by centrifugation were analyzed for their respective dry matter content. This allowed for the total dry mass in the original paste to be determined, as well as the amount of water-soluble components. The following Table 6 displays these results.

As can be seen from Table 6, the original fermentation product contains approximately 57% dry matter. Directly determining the dry matter content of the fermentation product led to an overestimation of this value. The method used to determine these values was an automated infrared balance which, for the original product gave values for dry matter of 61.3% (at 80° C.) and 60.2% (at 140° C.). When this paste was diluted according to the first step of the process, a value of 57.3% (at 140° C., after correcting for the dilution) was obtained, this being closer to the total amount of dry mass recovered during the separation. The original paste itself is probably too hygroscopic and/or bulky to effectively release all of its water. When, through diluting, less actual dry matter is analyzed, it is expected that comparatively more water would evaporate and a more accurate reading is obtained.

From the dry matter in the original fermentation product and the above data, the composition and phase distribution of the crude sophorolactone composition and of the dispersion were estimated as summarized in Table 7.

The dispersion consists of the solid, water insoluble, lactone and an aqueous phase with solvated lactone, water soluble partially acetylated lactone and sophorolipids in acid form as well as various salts, sugars and colored components. Approximately 30% can be separated as insoluble lactonic sophorolipids, i.e. sophorolactones. The remaining 70% are almost all to be found in the first three wash liquors, roughly distributed as 80/17/3. This remaining 70% are both water-soluble components as well as water-insoluble lactone as evidenced earlier by HPLC in Example 8.

TABLE 6

| Liquid phase determinations | | | | |
|---|---|---|---|---|
| Parameter | Amount (g) | % dry mass ($^m/_m$) | dry mass (g) | normalized[a] |
| Wash water 1 | 2160 | 17.1 | 370 | 31.1 |
| Wash water 2 | 2180 | 3.71 | 81 | 6.8 |
| Wash water 3 | 2260 | 0.58 | 13 | 1.1 |
| Wash water 4 | 2170 | 0.00 | 0 | 0 |
| Wash water 5 | 2320 | 0.00 | 0 | 0 |
| Total (water-soluble) | — | — | 464 | 39.0 |
| paste 5 | 593 | 35.3 | 210 | 17.6 |
| Total | — | — | 674 | 56.6 |

[a]normalization of the value for $m_{paste\ 0}$ to 100 and rounded

It is therefore postulated that the wash water is a ternary system consisting of water, water-soluble components (acid sophorolipids and other amphiphilic components in the medium) that solubilize the insoluble lactone and the lactone itself, with the ratio between the latter two remaining constant irrespective of the amount of water.

In performing the separation cycles, it was observed that the drop in viscosity and amount of associated water-soluble components had a direct impact on the amount of associated liquid. This impact is most notable for the first cycle, where the greatest difference in associated liquid is observed, i.e. between the original fermentation product and the paste obtained after the first cycle.

This is the result of a decrease in both the concentration of water-soluble emulsifiers, thus reducing the amount of water remaining associated with the insoluble lactone, and the accompanying reduction in viscosity which also facilitates the release of more water under the same centrifugation conditions. The 1:1 minimum dilution ratio previously established for the decantation technique also holds for centrifugation. It may be advantageous to re-use the water wash water.

TABLE 7

Composition and phase distribution of the crude sophorolactone composition and of the dispersion

| Component | % ($^w/_w$) | Phase (at T < 30° C.) | |
|---|---|---|---|
| Water | 50-55 | 50-55 | Liquid (as brown, clear solution) |
| Water soluble components from the fermentation medium | 0-5 | 0-5 | |
| Water soluble sophorolipids (=sophorolipids in acid form) | 10 | 10 | |
| Lactone form | 30 | 15 | |
| | | 15 | Solid (as white precipitate) |

Example 12

Previous attempts of obtaining crystalline sophorolipids from a crude sophorolactone composition containing considerable amounts of residual fatty acid failed. Such sophorolipid mixtures among others were obtained from fermentations that had to be terminated prematurely or when the oil feeding rate exceeded the consumption rate and accumulation of fatty acids had occurred. In order to define the maximal fatty acid content for optimal lactone isolation the following experiment was set up.

A sample of 171 g sophorolipid paste was dispersed in 342 g water as described previously, the sophorolipid concentration of 333 g/l approximating that of a typical fermentation broth. This dispersion contained 89 gram sophorolipids of which 26 g could be isolated as lactone. To this dispersion 0.45 gram up to 10.7 gram was added of a fatty acid mixture ("FA" in Table 8 below, Radiacid 0223 of vegetable origin, similar in composition as the vegetable oil used for feeding) to observe the lactone separation and the characteristics of the supernatant. The dispersion was vigorously stirred and an additional amount of fatty acids was added (e.g. another 0.45 g to obtain the second row in the table below, another 0.89 g for the third row, etc).

TABLE 8

Observations regarding lactone separation and supernatant characteristics

| m(FA) (g) | % FA (to SL total) | % FA (to total) | Lactone separation? | Supernatant |
|---|---|---|---|---|
| 0.45 | 0.5 | 0.09 | Yes | Clear; 1 phase |
| 0.90 | 1.0 | 0.18 | Yes | Clear; 1 phase |
| 1.79 | 2.0 | 0.35 | Yes | Clear; 1 phase |
| 3.57 | 4.0 | 0.70 | Yes | Turbid; 1 phase |
| 5.36 | 6.0 | 1.04 | Yes (but reduced) | Clear; 2 phases |
| 7.15 | 8.0 | 1.39 | Yes (but reduced) | Clear; 2 phases |
| 8.92 | 10.0 | 1.74 | Yes (but reduced) | Clear; 2 phases |
| 10.70 | 12.0 | 2.09 | No | Clear; 2 phases |

The formation of a dark liquid intermediary phase was observed when the fatty acid content exceeded 4% as calculated on the total amount of sophorolipids (SL) in the dispersion. This corresponds to 0.7% residual fatty acid in the fermentation broth (3.57 g added to a reconstituted broth of 513 g). The turbid supernatant at 4% indicates a similar density between the aqueous phase and the liquid intermediary phase resulting from sufficient amounts of low density fatty acid to start interfering with the separation of the lactone, by solubilizing part of the lactone fraction. The isolation of lactone becomes impossible when the broth contains 2% fatty acid or more.

Example 13

Figure 6:
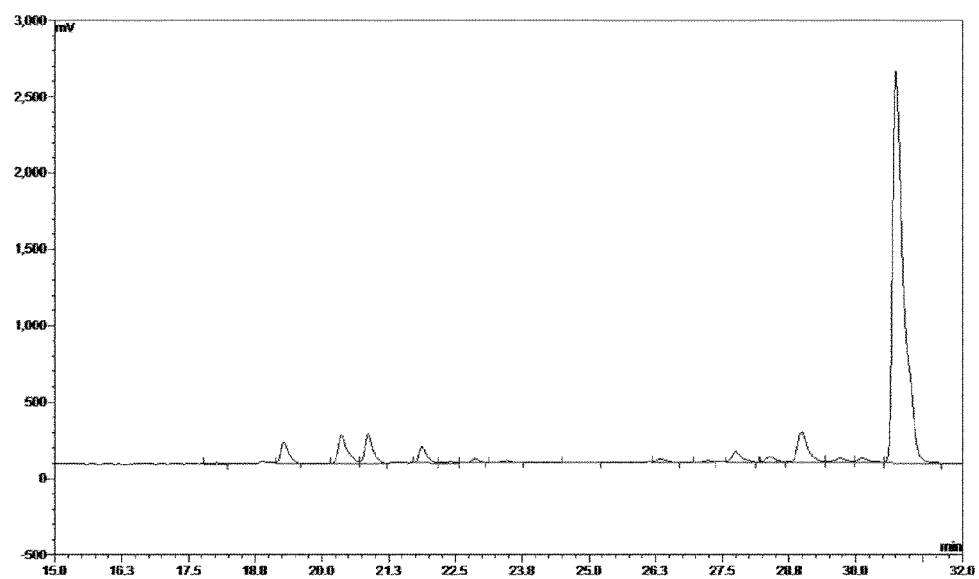
FIG. 6 is a graphic representation of a chromatogram recorded for the experiment described in Example 13. The chromatogram was recorded on a mixture of sophorolipids out of which solid lactonic sophorolipids could be obtained through dispersion in water.

The minimal relative lactone content of a sophorolipid mixture has to be greater than 30% by weight in order for the successful removal of lactonic sophorolipids by dispersion in water. Such was determined by saturating a mixture of water-soluble sophorolipids with lactonic sophorolipids. The watery phase was then analyzed by reverse phase high performance chromatography and it was found that the lactone sophorolipid content of the watery phase increased to a value of 30% by weight, relative to the total sophorolipid amount. Therefore it follows that any sophorolipid mixture containing an amount of lactone form, this form must be present in excess of 30% by weight expressed relative to the total amount of sophorolipids, in order for a portion of this lactone form to precipitate as a solid. The chromatograms shown in FIG. 5 and FIG. 6 show the analysis of a water-soluble mixture of sophorolipids which is saturated with the lactone form (FIG. 5) and a sophorolipid mixture out of which it is possible to precipitate part of the lactonic sophorolipids (FIG. 6).

Example 14

The sophorolactone obtained from examples 8-11 by crystallization followed by decantation or centrifugation; had a dough-like consistency and still contained approximately 50-65% water depending on the isolation technique. A simple method for decreasing the water content of these lactonic sophorolipids was to heat them. The purer lactonic sophorolipids liquefied and settled to form a separate phase at temperatures in excess of 45° C. The separate phase was isolated. After isolation it was transferred to storage, especially for large volumes, or left to solidify for easy removal of the small volume of supernatant watery phase. Afterwards, the lactone was obtained as a white solid which contained approximately 15% of water. Analysis of the watery phase indicated that less than 1% of the lactone remained dispersed. Further air drying of such material and grinding resulted in a non-sticky powder with a melting point of 79° C.

Example 15

During the settling of a crude sophorolactone composition in the fermenter, small amounts of yeast and cell fragments are entrapped in the drained precipitate. After settling, a border layer of yeast cells on top of the warm sophorolipids is formed. Part of this layer may also be drained along with the sophorolipids, both sources resulting in small amounts of particulates in the product. In order to prevent particulates to end up among the lactone crystal fraction several filtration techniques were tested and compared.

In order to check sufficient removal of cells and cell fragments a 5 wt % solution of raw sophorolactone composition was made in 0.36 N KOH and measured at 666 nm (zeroed to water) using a path length of one inch. For the crude unfiltered sophorolactone composition optical density values were obtained between 0.5 and 0.7. A value of less than 0.2 indicates sufficient removal of cell fragments.

The inventors have found that the small yeast fragments can be removed by dead-end filtration. This filtration is suitable for use on the crude sophorolactone composition in the liquid state drained from the fermenter.

Use of a temperature of approximately 60° C. ensured that a viscosity was obtained suitable for filtration. This is illustrated in Table 8, wherein viscosity measurements using a Brookfield DV-II+ Pro Viscosimeter are listed. Results are expressed in centipoise (cP). Table 8 further lists the spindle used as well as velocity, expressed in rotation per minute (rpm). The temperature was gradually increased in increments of 10° C., to a reach a temperature of 40° C. to 90° C.

TABLE 9

Viscosity measurements

| T (° C.) | Viscosity (cP) | Spindle | Velocity (rpm) |
|---|---|---|---|
| 40 | 422 | 34/31 | 100/50 |
| 50 | 230 | 31 | 50 |
| 60 | 136 | 31/18 | 100/20 |
| 70 | 82 | 18 | 20 |
| 80 | 57 | 18 | 20/50 |
| 90 | 39 | 18 | 50 |

Example 16

The lactone obtained in Example 10 was partially hydrolysed in degrees ranging from 0 to 2 equivalents using potassium hydroxide. Partial alkaline hydrolysis in this context implies that less than 3 mol KOH were added per mol lactone. As a consequence only part of the 3 ester bonds, i.e. the lactonic bond and the two acetyl ester bonds, was hydrolysed and a mixture of various sophorolipids formed.

For example one liter of a 35% active matter 0.7 partial hydrolysate was prepared as follows:

1) the lactone content of 250 g crude sophorolactone composition (70% dry matter) as drained from the bottom of the fermenter was dispersed in 750 g water (1 part sophorolactone composition versus 3 parts water), washed three times and centrifuged. This yielded 140 g wet lactone with a dry matter of 33%. The crude mix thus contained 26% insoluble lactone.

2) 500 g crude mix contains 92 g insoluble lactone or with a MW of 689 this corresponds to 0.13 mol. A 0.7 equivalents partial hydrolysate thus requires 0.7*0.13 mol KOH or 0.7*0.13*56.11 g $KOH_{100\%}$ or 10.5 g $KOH_{50\%}$. To the 500 g crude mix, 10.5 g $KOH_{50\%}$ and 489.5 g water was added. This mixture was homogenized and allowed to react at 80° C. for 4 hours, 60° C. for approximately 6 hours, or for 3 days at 45° C. until a clear solution was obtained with a pH of 6.5 or less, the pH typically stabilized at 5.5 and a clear liquid layer settled from the reaction mixture. The mixture now contained sufficient water soluble sophorolipids, i.e. sophorolipids in acid form, to solubilize the remaining lactone in a separate aqueous phase.

When less than 0.7 mole equivalents KOH were added or when the reaction was terminated prematurely a solid white residual lactone interphase between the two liquid phases was formed. When adding more than 1.0 equivalent KOH, an excess of water soluble sophorolipids prevented the settling of a second aqueous phase. This suggests a balance exists between the water soluble and insoluble sophorolipids in acid conditions in which a second aqueous phase is formed with a constant water content of 50%.

Figure 7:
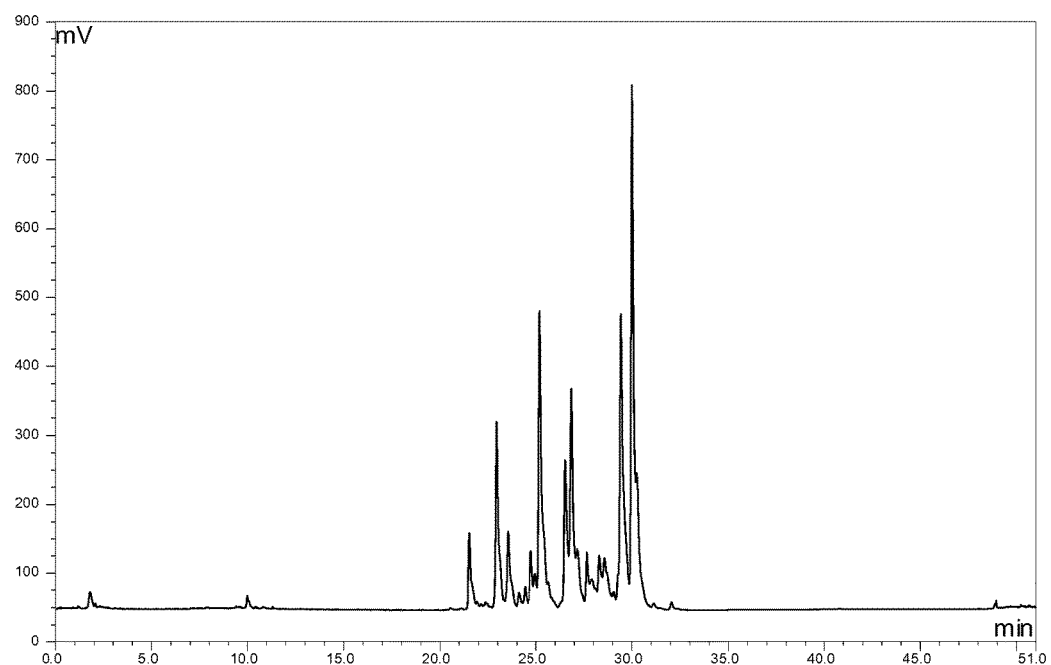
FIG. 7 is a graphic representation of a chromatogram recorded for the experiment described in Example 16 (bottom phase, 1% in ethanol, 20 µl injection volume).

The spontaneous separation ensured that practically all sophorolipids were present in the bottom layer, whereas the potassium acetate formed in the hydrolysis was present in the top layer. This separation was enhanced further when the pH of the upper layer was lowered to 4.0. Further lowering of the pH did not result in additional separation. The chemical composition of the bottom layer after partial hydrolysis with 0.7 mol equivalent KOH is depicted in FIG. 7. The chemical structure of the partial hydrolysates was characterized using HPLC-ELSD.

Hardly any potassium acetate was present in the bottom layer and a substantial amount of lactone, although less than in the first wash water (Example 8). This light colored material, rich in lactone, could easily be formulated in a cleaning product by combining it with other surfactants.

Table 10 summarizes the data for all hydrolysates. From the results in Table 10 it follows that the double acetylated lactone form gradually disappears upon partial hydrolysis and from 0.8 equivalents onwards some fully hydrolysed material was present.

The static surface tension of the partial hydrolysates obtained in the above described experiment was measured according to the pending drop method on a Krüss DSA100 tensiometer. The results are provided in Table 10. From this table it can be concluded that the 0.6 equivalent partial hydrolysate was most effective in lowering the surface tension.

TABLE 10

Summary of chromatographic data for the hydrolysates obtained in Example 15.

| | | | | Retention time | | | | |
|---|---|---|---|---|---|---|---|---|
| | MW | ITC | Inge | corr | 0 eq | 0.6 eq | 0.7 eq | 0.8 eq | full |
| C18:1/0 Ac/OOH | 622 | 19.22 | 19.85 | 0.63 | | | | 19.84 | 19.86 |
| C18:1/1 Ac/OOH | 664 | 19.87 | 20.37 | −1.41 | | 21.26 | 21.27 | 21.28 | |
| ? | | | | | | | | 21.91 | |
| C18:1/2 Ac/OOH | 706 | 22.62 | 23.12 | 24.02 | | | | 23.18 | |
| ? | | | | | | 23.80 | 23.81 | 23.84 | |
| ? | | | | | | 25.31 | 25.31 | 25.37 | |
| ? | | | | | | 25.74 | 25.74 | 25.90 | |
| ? | | | | | | 28.99 | 29.00 | 29.06 | |
| C18:1/2 Ac/Lac | 688 | 29.37 | 29.79 | 0.42 | 29.84 | 29.75 | 29.76 | 29.81 | |

TABLE 11

Measurements of static surface tension

| Conc. (ppm) | water | SL18 lactone | SL18 fully hydrolysed | SL18 0.6 eq | SL18 0.7 eq | SL18 0.8 eq | SL 18 1 eq | SL18 1.5 eq | SL18 2 eq |
|---|---|---|---|---|---|---|---|---|---|
| 10 | 71.26 | 71.00 | 71.50 | 51.72 | 54.33 | 61.53 | 70.71 | 69.94 | 70.95 |
| 50 | 71.26 | 66.21 | 67.95 | 39.16 | 44.11 | 55.62 | 56.41 | 58.17 | 60.42 |
| 100 | 71.26 | 63.02 | 65.52 | 34.84 | 38.03 | 47.39 | 46.37 | 48.27 | 50.36 |
| 250 | 71.26 | 47.67 | 62.29 | 33.92 | 34.29 | 39.41 | 36.85 | 38.39 | 39.56 |
| 1000 | 71.26 | 36.69 | 56.04 | 33.88 | 33.99 | 34.09 | 34.20 | 35.17 | 36.47 |
| 2000 | 71.26 | 36.26 | 53.50 | 33.82 | 33.99 | 34.12 | 34.54 | 35.60 | 36.57 |
| 5000 | 71.26 | 35.85 | 49.69 | 33.95 | 34.19 | 34.31 | 34.87 | 36.17 | 37.41 |
| 10000 | 71.26 | 35.33 | 48.31 | 34.22 | 34.27 | 34.38 | 35.12 | 36.27 | 37.99 |
| 25000 | 71.26 | 35.54 | 47.21 | 34.14 | 34.30 | 34.54 | 35.30 | 36.41 | 37.86 |
| 50000 | 71.26 | 35.14 | 46.07 | 33.99 | 34.15 | 34.46 | 35.16 | 36.25 | 37.48 |

Example 17

A sophorolipid lactone sample obtained from the experiment described in Example 8 was centrifuged, spread out on Torck paper and allowed to air dry. The resulting solid was crushed with a coffee mill to a fine powder and dried further with compressed air to >98 wt %. This powder was compared as to its efficiency in automatic dishwashing versus a low foaming alkylpolyglucoside, in particular Simulsol AS48, available from Seppic SA, at equal active matter content. The surfactant was formulated in the following base formula: 9.43% sodium citrate.$2H_2O$; 3.08% percarbonate; 2.72% sodium carbonate; 2.05% sodium silicate; 1.05% sodium bicarbonate; 0.77% sodium polyaspartate; 0.62% tetra acetyl ethylene diamine (TAED)+1.4% surfactant. 20 gram of the base formula was dosed in a ZDF211 dishwasher. Program D 50° C. eco was run.

In the automatic dishwasher 7 types of soil plates (available from CFT, Vlaardingen, The Netherlands) mounted in a stainless steel holding frame were inserted. The results obtained are summarized in Table 12.

As evidenced from the above soil removal rates, sophorolipid lactone, although virtually insoluble as such, was superior to Simulsol AS48. It is assumed the alkaline pH of about 9.8 caused in situ hydrolysis providing an efficient surfactant.

Example 18

A stock solution was prepared containing 7.5% partially hydrolysed sophorolipids, 5% surfactant (Glucopon 215), 3% ethanol and 0.5% glycerol monocaprylate. The pH of the formulation was set at 6.3 using citrate and lactic acid.

This stock solution was divided into five equal portions, denominated in Table 13 as Sample I to V. To four of the samples, in particular to samples II-V, increasing levels of oleic acid were added to simulate the effect of residual substrate on finished product stability. The samples were then divided in three. These sub-samples were stored for 4 weeks at 4° C., 20° C. or 40° C. At the end of the four weeks, the sub-samples were visually inspected and rated with regard to their stability. The results are summarized in Table 13.

The samples were inspected visually. Stable samples (marked as "OK") remained completely homogeneous upon

TABLE 12

Stain removal efficacy for Simulsol AS48 compared to lactone for a series of stains.

| | Stain | | | | | | |
|---|---|---|---|---|---|---|---|
| | Cheese DM06 | Egg yolk/ milk DM31 | Mix starch DM77 | Coffee DM81 | Tea DM11 | Red wine DM51 | Chocolate DM75 |
| Simulsol AS48 | | | | | | | |
| average Rs | 25.4 | 44.8 | 35.9 | 69.8 | 61.6 | 56.3 | 17.8 |
| average Rw | 40.0 | 51.2 | 39.2 | 77.9 | 75.2 | 72.2 | 24.0 |
| soil removal | 14.6 | 6.4 | 3.3 | 8.1 | 13.6 | 16.0 | 6.2 |
| Lactone | | | | | | | |
| average Rs | 25.0 | 45.1 | 36.0 | 70.2 | 61.1 | 55.3 | 17.8 |
| average Rw | 41.9 | 52.0 | 37.6 | 77.5 | 75.7 | 72.4 | 24.9 |
| soil removal | 16.9 | 6.8 | 1.6 | 7.3 | 14.6 | 17.1 | 7.1 |

Rs = Y reflection value for soiled; Rw = Y reflection value for washed storage under the described conditions, with no distinct liquid layers being formed, no phase separation or sedimentation as opposed to unstable sample (marked as "NOK").

TABLE 13

Storage stability data of samples with varying levels of oleic acid, measured at different temperatures.

| Sample | % oleic acid | 4° C. | 20° C. | 40° C. |
|--------|--------------|-------|--------|--------|
| I      | 0            | OK    | OK     | OK     |
| II     | 0.2          | OK    | OK     | OK     |
| III    | 0.4          | NOK   | OK     | OK     |
| IV     | 0.6          | NOK   | OK     | OK     |
| V      | 0.8          | NOK   | OK     | NOK (droplets) |

As evident from Table 13 residual substrate levels affect storage stability of a cleaning product. For this particular formula it is recommendable to keep residual substrate levels as low as 0.2% on the end product, or 2.7% on the sophorolipid. Formulations not containing a second surfactant, such as Glucopon 215 in this example, will be even more sensitive to residual substrate levels.

Example 19

Sophorolactone compositions as obtained in Examples 1 to 7 or sophorolactone as obtained in Examples 8 to 15 were completely hydrolysed by adding 3.2 equivalents KOH and water to obtain a 10% dry matter solution. The reaction mixture was heated to 50° C., stirred for 10 minutes and passed twice over a glass fiber filter. The mixture was heated to 80° C. during 4 hours to complete the hydrolysis and obtain the deacetylated acid sophorolipid.

The pH of the mixture was adjusted to pH 1.5 using 37% HCl and left to precipitate overnight. The acid sophorolipids were separated from the supernatant salt solution (KCl and potassium acetate) by centrifugation. The sophorolipids were washed and redispersed twice with 1% HCl, collected by centrifugation, air dried and ground to a white powder.

Example 20

Residual substrate determination was advantageously carried out as follows: a sophorolactone sample of 200 g was liquefied by warming it to 60° C. It was then extracted twice with an equal volume of n-hexane in a separation funnel. Subsequent evaporation of the pooled extracts yielded the bulk of residual free fatty acids. The residual free fatty acid level was then determined by weighing the amount of residue obtained and calculation of the amount obtained relative to the original sample weight. Having the sophorolipids in a liquid phase greatly increased the speed of phase separation from about one day, using solid sophorolactone as starting material, to half an hour, using the liquefied material. It was also found that using cyclohexane instead of n-hexane resulted in a ω-extraction of an unacceptable amount of sophorolactone, where n-hexane did not.

Example 21: Effect of Too High Level of Residual Free Fatty Acid Level in Fermentation Broth Three flasks containing 1500 ml pre culture medium were each inoculated with *Candida bombicola*. After 72 h incubation at 25° C. the content of the three flasks was pooled for inoculation of the seed tank. The development and morphology of the inoculum shake flasks was in line with the results of the lab scale experiments. Limited foaming was observed till approximately 36 hours. No foreign growth was detected.

The seed fermentation was inoculated by approximately 4.5 l, 72 h old, shake flasks material. After a somewhat slow start, the seed tank developed well. After 66 hours, still in the stationary phase, approx. 1 m$^3$ of the seed tank material was used to inoculate the main fermenter. No foreign growth was detected.

The main fermentation was inoculated by approximately 1 m$^3$ of the 2.2 m$^3$ seed tank material, of 66 hours of age. During the process non-sterile rape seed oil was continuously fed whereas glucose was added in shots. Within the window of 198-216 hours for operational reasons, the main fermentation was terminated at 204 hours after inoculation. The broth weight at this time was determined at approximately 41 tons, 31% by volume of which was a sophorolipid mixture settling upon heating.

The dosing of glucose was based on the actual residual glucose concentration of the broth, which during the total course of fermentation did not drop below 60 g/l. Divided over 5 shots 5639 kg pure glucose was dosed. Together with a batch dosing of 2593 kg in total 8232 kg of glucose was added to the process.

Due to a defective process control, the rape seed oil feeding was not controlled based on the maximum allowable level of 10 g/l fatty acid content of the broth. Feeding started directly after inoculation, in total 6300 kg of rape seed oil was added. Eight hours before the end of fermentation the rape seed oil feed was stopped.

The material obtained stayed liquid. Sophorolactone could not be selectively retrieved from the reaction broth without use of organic solvents.

Another aberrant observation was the water content of 45%. Raw sophorolactone from a method according to an embodiment of the invention typically results in raw sophorolactone with a water content of 35-40%.

Measurements of the residual substrate in the end product using the method of example 21, showed that the fatty acid content of the broth, was at least 4%.

Example 22: Storage Stability Test

A sample was prepared of 10 g sophorolactone and 90 g ethyllactate and another sample of 10 g sophorolactone and 90 g isoamyl lactate. Both samples were split in 50 ml samples and stored at 4° C. and at 40° C. respectively. After 2 months of storage they were analyzed with HPLC-ELSD. The results are as illustrated by the chromatograms depicted in FIG. 7 and FIG. 8. After 2 months of storage at either 4° C., result depicted in FIG. 7, or 40° C., result depicted in FIG. 8, of this non-aqueous sophorolactone solution only a negligible hydrolysis of lactone material occurred as evidenced by an acid sophorolipid peak appearing at 30.5 min in the grey overlay graph. This peak represents less than 1% of the total peak area.

What is claimed is:

1. A process for the selective production of sophorolactone in the absence of an organic solvent, comprising the steps of:
   (a) pre-cultivating cells of a *Candida* species capable of producing sophorolactone, in the absence of an oily substrate until a stationary growth phase is obtained;
   (b) cultivating said pre-cultivated cells in an aqueous medium which comprises at least one fermentable sugar and at least one fermentable substrate; wherein the fermentable substrate comprises a triglyceride, whereby said fermentable sugar, said fermentable substrate and said pre-cultivated cells are present in an amount and conditions such that the cells metabolize the fermentable sugar and the fermentable substrate, thereby forming sophorolactone and fatty acid;

(c) continuously feeding said fermentable substrate to said cells thereby suppressing the formation of fatty acid and keeping fatty acid levels in the reaction mixture below 10 g/L, resulting in the crystallization of at least part of the sophorolactone present in the reaction mixture;

(d) warming the reaction mixture to a temperature between 60° C. and 90° C., thereby melting the sophorolactone crystals;

(e) allowing the molten sophorolactone to settle and to provide a crude sophorolactone composition;

(f) removing the crude sophorolactone composition from the remainder of the reaction mixture without the use of an organic solvent;

(g) cooling the crude sophorolactone composition thereby producing a solid sophorolactone; and (h) dispersing the obtained solid of step (g) in water at a temperature of 5-25° C., wherein a mass ratio of water to the obtained solid is from 0.5:1 to 15:1, thereby obtaining an aqueous dispersion of sophorolactone crystals.

2. The process according to claim 1, further comprising the steps of:

(i) separating said sophorolactone crystals from the water;

(j) optionally repeating the dispersion and separation steps (h) and (i), thereby keeping the temperature of the water below 40° C.; and finally (k) drying the resulting sophorolactone crystal composition thereby providing dried sophorolactone.

3. The process according to claim 2, wherein prior to said drying step (k) and after dispersion and separation step(s) of (h) and (i) of claim 2, water is removed from the sophorolactone crystals by melting the sophorolactone crystals to a temperature between 35° C. and 55° C., thereby providing a lower layer comprising sophorolactone and an upper layer of supernatant water; and separating the lower layer from the upper layer.

4. The process according to claim 3, wherein drying is by spray drying, drum drying, convection drying, thin film evaporation, vacuum drying, flaking, extruding or casting.

5. The process according to claim 1, wherein the water separated from the crystals, is re-used in said dispersing step (h).

6. The process according to claim 1, wherein the crude sophorolactone composition separated off from the remainder of the reaction mixture in step (f) is in the form of an aqueous sophorolipid mixture comprising at least 30 wt %, expressed on the dry matter content of the aqueous sophorolipid mixture.

7. The process according to claim 1, wherein the fermentable sugar and fermentable substrate in step (b) are fed to the pre-cultivated cells in a fed batch mode.

8. The process according to claim 1, wherein the fermentable substrate further comprises corn steep liquor.

9. The process according to claim 1, further comprising the step of filtering the crude sophorolactone composition separated off from the reaction mixture in step (f) by depth filtration.

10. The process according to claim 1, wherein the fermentable substrate further comprises a carbon chain length lower than C14 and the fermentation medium in step (b) comprises cells of a *Candida* species modified to improve the conversion of said substrate into sophorolactone, wherein the *Candida* species is *Candida bombicola* mutant strain M18, M30 or M33.

11. The process according to claim 1, further comprising the step of filtering the crude sophorolactone composition separated off from the reaction mixture in step (f) by dead-end filtration.

* * * * *